United States Patent [19]

Nakahara et al.

[11] Patent Number: 4,898,688
[45] Date of Patent: Feb. 6, 1990

[54] POLY(2,2,6-TETRAMETHYL PIPERIDYL AMINO)-1,3,5-TRIAZINES AS STABILIZERS FOR SYNTHETIC POLYMER COMPOSITIONS

[75] Inventors: Yutaka Nakahara, Okegawa; Etsuo Tobita, Urawa, both of Japan

[73] Assignee: Adeka Argus Chemical Co., Ltd., Urawa, Japan

[21] Appl. No.: 139,525

[22] Filed: Dec. 30, 1987

Related U.S. Application Data

[62] Division of Ser. No. 884,146, Jul. 10, 1986, abandoned.

[30] Foreign Application Priority Data

Jul. 17, 1985 [JP]  Japan .............................. 60-157727

[51] Int. Cl.[4] .............................................. C09K 15/18
[52] U.S. Cl. ............................ 252/400.24; 252/403; 252/400.1; 252/400.24; 252/400.52
[58] Field of Search ................ 252/403, 400.1, 400.24, 252/400.52

[56] References Cited

U.S. PATENT DOCUMENTS

| | | | |
|---|---|---|---|
| 3,925,376 | 12/1975 | Chalmers et al. | 524/100 X |
| 4,165,592 | 7/1979 | Evans et al. | 524/100 X |
| 4,191,683 | 11/1980 | Brunetti et al. | 252/403 |
| 4,234,728 | 3/1980 | Rody et al. | 524/100 X |
| 4,263,434 | 4/1981 | Cassandrini et al. | 524/101 |
| 4,288,593 | 8/1981 | Rody | 524/100 X |
| 4,294,963 | 10/1981 | Rody | 524/100 X |
| 4,317,911 | 3/1982 | Rasberger et al. | 524/101 X |
| 4,321,374 | 3/1982 | Morimura et al. | 524/100 X |
| 4,524,165 | 6/1985 | Musser et al. | 524/99 |

Primary Examiner—John F. Terapane
Assistant Examiner—Valerie Fee

[57] ABSTRACT

Stabilizers for synthetic polymer compositions are provided which are poly(2,2,6,6-tetramethyl piperidyl amino)-1,3,5-triazines having the formula:

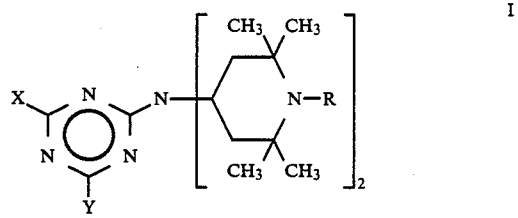

in which:

R is selected from the group consisting of hydrogen; alkyl, alkenyl, cycloalkyl, hydroxyalkyl and alkoxy having from one to about twelve carbon atoms; acyl having from about one to about twelve carbon atoms; and oxyl;

X and Y are each selected from the group consisting of

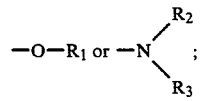

wherein:

$R_1$ is selected from the group consisting of alkyl, hydroxyalkyl and alkylenealkoxy having from one to about twelve carbon atoms; cycloalkyl having from three to about twelve carbon atoms; and aryl having from six to about eighteen carbon atoms;

$R_2$ and $R_3$ are selected from the group consisting of hydrogen; alkyl having from one to about twelve carbon atoms; cycloalkyl having from three to about twelve carbon atoms; and aryl having from six to about eighteen carbon atoms; and $R_2$ and $R_3$ taken together as a five to six member ring including the nitrogen atom in the ring; and

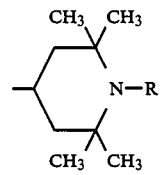

5 Claims, No Drawings

POLY(2,2,6-TETRAMETHYL PIPERIDYL AMINO)-1,3,5-TRIAZINES AS STABILIZERS FOR SYNTHETIC POLYMER COMPOSITIONS

This is a division of application Ser. No. 884,146, filed July 10, 1986 abandoned.

Synthetic polymers such as polyethylene, polypropylene and polyvinyl chloride undergo degradation upon exposure to ultraviolet light, resulting in discoloration, deterioration in mechanical strength and embrittlement. Consequently, various types of stabilizers have been incorporated with these polymers to inhibit such deterioration. However, many of the available stabilizers are unsatisfactory in stabilizing effect, are unstable to heat and subject to oxidation, and are easily extracted from the synthetic polymer composition by water and organic solvents. Some of the available stabilizers impart color to the polymer compositions.

Murayama et al U.S. Pat. No. 3,640,928, patented Feb. 8, 1972, discloses the stabilization of synthetic polymers against photo- and thermo-deterioration thereof by incorporating therein a piperidine derivative having the general formula

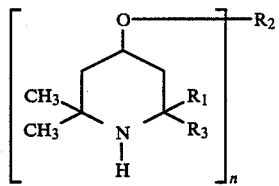
(I)

The 2,2,6,6-tetramethylpiperidyl compounds are particularly desirable because they do not impart color, and therefore are widely used. However, these compounds are easily volatilized from the polymer composition at elevated temperature, such as during processing, and are also extracted by water. In addition, many are unsatisfactory in their stabilizing effectiveness.

Triazines containing 2,2,6,6-tetramethyl piperidyl groups have a considerably improved heat stability and therefore are preferred for many uses.

Chalmers, Jack and Cook, U.S. Pat. No. 3,925,376 patented Dec. 9, 1975 provide piperidinyl 1,3,5-triazine compounds having the formula

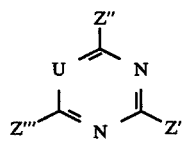
I and salts thereof, wherein U is —CH— or —N— and Z' is a residue having the formula

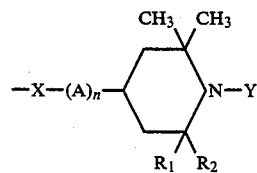
II wherein $R_1$ and $R_2$ are the same or different and each is a straight- or branched alkyl residue having from 1 to 12 carbon atoms, or $R_1$ and $R_2$ form, together with the ring carbon atom to which they are each bound, a cycloalkyl residue having from 5 to 12 carbon atoms; X is an —O—, —S— or

residue, wherein R is hydrogen, a straight or branched alkyl residue having from 1 to 20 carbon atoms or an aralkyl residue having from 7 to 12 carbon atoms; Y is O, hydrogen, a straight or branched alkyl residue having from 1 to 20 carbon atoms, an alkenyl or alkynyl residue having from 3 to 12 carbon atoms, an aralkyl residue having from 7 to 12 carbon atoms or the group

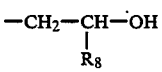

wherein $R_8$ is hydrogen, or a methyl or phenyl residue; n is 0 or 1; and A is —CH$_2$—, or the group

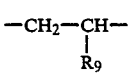

wherein $R_9$ is hydrogen or an alkyl residue having from 1 to 20 carbon atoms; Z" and Z''' are the same or different and each is a piperidine residue of formula II as hereinbefore defined, a halogen atom, a substituted amino group having the formula:

III wherein $R_3$ and $R_4$ are the same or different and each is hydrogen, a straight- or branched alkyl residue having from 1 to 20 carbon atoms, a cycloalkyl residue having from 5 to 12 carbon atoms, an aryl residue which is unsubstituted or substituted by one or more alkyl groups and having a total of from 6 to 18 carbon atoms or an aralkyl residue having from 7 to 12 carbon atoms; or $R_3$ and $R_4$, together with the nitrogen atom to which they are bound form a heterocyclic residue having 5 to 7 ring atoms; or Z" and Z''' are an hydroxy or ether group having the formula:

IV wherein $R_5$ is hydrogen, a straight- or branched-chain alkyl residue having from 1 to 20 carbon atoms, a cycloalkyl residue having from 5 to 12 carbon atoms, an aryl residue which may be unsubstituted or substituted by one or more alkyl groups, having a total of 6 to 18 carbon atoms or an aralkyl residue having from 7 to 12 carbon atoms; or Z" and Z''' are a thiol or thio ether group having the formula:

V wherein $R_6$ is hydrogen, a straight- or branched alkyl residue having from 1 to 20 carbon atoms, a cycloalkyl, having from 5 to 12 carbon atoms or a phenyl or benzyl residue.

Cassandrini and Tozzi, U.S. Pat. No. 4,086,204 patented Apr. 25, 1978 provide piperidinyl triazine polymers having the general formula:

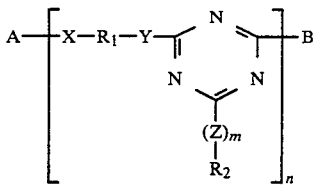

in which:

X, Y, Z the same or different, represent —O—, —S—,

with $R_3$ being hydrogen, a straight or branched chain alkyl having 1 to 18 C atoms, a cycloalkyl having 5 to 18 C atoms, a substituted or non-substituted aryl having 6 to 18 C atoms, an aralkyl having 7 to 18 C atoms, or $R_3$ represents a piperidine radical of the formula:

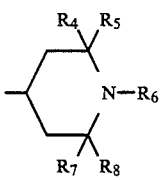

wherein each of $R_4$, $R_5$, $R_7$ and $R_8$ the same or different, are a $C_1$ to $C_6$ alkyl, and $R_6$ is hydrogen, O, a $C_1$ to $C_{18}$ straight or branched chain alkyl, a $C_2$ to $C_{18}$ alkenyl or alkynyl, or a $C_7$ to $C_{18}$ aralkyl;

$R_1$ is a $C_2$ to $C_{18}$ straight or branched chain alkylene, a $C_5$ to $C_{18}$ cycloalkylene, a $C_6$ to $C_{18}$ arylene, and a $C_7$ to $C_{18}$ aralkylene.

Furthermore, —X—$R_1$—Y— can be a bivalent radical of a heterocycle compound with 6 to 8 members having 2 nitrogen atoms; in such case X and Y are a disubstituted nitrogen atom respectively;

—X—$R_1$—Y— can be also replaced by the radical

in which $R_9$, $R_{10}$ the same or different, are H, a $C_1$ to $C_{12}$ alkyl, a $C_5$ to $C_{12}$ cycloalkyl, a $C_6$ to $C_{12}$ aryl, a $C_7$ to $C_{12}$ aralkyl;

m is either 0 to 1;

$R_2$ represents —H, —Cl, —Br, —OH, a straight or branched chain $C_1$ to $C_{18}$ alkyl, a $C_5$ to $C_{18}$ cycloalkyl, a substituted or not substituted $C_6$ to $C_{18}$ aryl, a $C_7$ to $C_{18}$ aralkyl, a piperidine radical of formula (II), or $R_2$ represents the radical

in which $R_{11}$, $R_{12}$ are hydrogen, $C_1$ to $C_{12}$ alkyl, $C_5$ to $C_{12}$ cycloalkyl, $C_6$ to $C_{12}$ aryl, or $C_7$ to $C_{12}$ aralkyl;

when m is 1, the radical $R_2$—Z— can be the same as —X—$R_1$—YH, where X, Y, $R_1$ have the meaning above indicated.

n is an integer from 2 to 200;

A and B represent the terminal groups. By the term "terminal groups" it is meant the terminal groups of a molecule of formula (I) resulting from the polymerization reaction, which generally are a residue of functional groups. The nature of said residue depends on the reaction conditions, the nature and amount of the reactants used in the reaction, for example, as it is known to one skilled in the art. Said residue is preferably H for A and —X—$R_1$—YH for B, in that it is preferred using an excess of bifunctional compound in the reaction for controlling the molecular weight.

In formula (I) there is the condition that either radical —X—$R_1$—Y— or —(Z)$_m$—$R_2$, or both contain at least one piperidine radical of formula (II).

Cassandrini and Tozzi, U.S. Pat. No. 4,108,829 patented Aug. 22, 1978, provide piperidinyl 1,3,5-triazine compounds having the general formula (I):

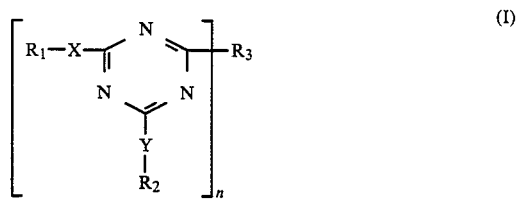

wherein $R_1$, $R_2$ same or different are hydrogen, hydroxyl, a straight or branched chain $C_1$ to $C_{18}$ alkyl, a $C_5$ to $C_{18}$ cycloalkyl, a substituted or not substituted $C_6$ to $C_{18}$ aryl, a $C_7$ to $C_{18}$ aralkyl, or a piperidine radical of formula (II)

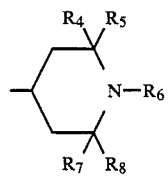

in which $R_4$, $R_5$, $R_7$, $R_8$ same or different, are each a $C_1$ to $C_6$ alkyl and $R_6$ is H, O, a $C_1$ to $C_{12}$ alkyl, a $C_2$ to $C_{12}$ alkenyl or alkinyl;

$R_1$, $R_2$ can also represent a group

in which $R_9$, $R_{10}$ same or different, are each hydrogen, $C_1$ to $C_8$ alkyl, $C_5$ to $C_8$ cycloalkyl or $C_6$ to $C_8$ aryl;

X, Y same or different represent —O—, —S—,

$R_{11}$ being H, a straight or branched chain $C_1$ to $C_{18}$ alkyl, $C_5$ to $C_{18}$ cycloalkyl, $C_6$ to $C_{18}$ aryl, $C_7$ to $C_{18}$ aralkyl, or a piperidine radical of formula (II).

The radicals $R_1$—X—, $R_2$—Y—, taken as a single substituent group, can also be radicals from nitrogenous heterocyclic compounds having 5 to 8 members, linked to the triazine ring by a bisubstituted nitrogen atom of said radical. They can also represent Cl— or Br—;

n is an integer from 2 to 6;

$R_3$ is a n-valent residue deriving from a polyalcohol, a polymercaptan or a polyamine by reaction of the active H atoms thereof with a halogen atom of a monohalogen triazine;

$R_3$ can be a radical of type $R_{12}$—$(Z)_n$—, wherein $R_{12}$ is a n-valent, $C_1$ to $C_{18}$ aliphatic, $C_5$ to $C_{18}$ cycloaliphatic or $C_6$ to $C_{18}$ aromatic radical, and Z is —O—, —S—,

wherein $R_{11}$ has the same meaning as previously indicated.

When n=2, the radical $R_3$ can also be the bivalent radical of a nitrogenous heterocyclic compound having 6 to 8 members, the bisubstituted nitrogen atoms of which are linked to a triazine ring; when n=2, $R_3$ can also be a radical of type

in which $R_{13}$, $R_{14}$ same or different, are each hydrogen, $C_1$ to $C_{12}$ alkyl, $C_5$ to $C_{12}$ cycloalkyl, $C_6$ to $C_{12}$ aryl, $C_7$ to $C_{12}$ aralkyl or a piperidine radical of formula (II).

When n=3, 4, 5, 6, $R_3$ can also be a radical of type

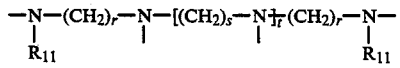

in which $R_{11}$ has the same meaning as previously indicated; r, s, same or different, are an integer from 2 to 6 and t is an integer from 0 to 3.

In formula (I) there is the condition that at least in one of the radicals $R_1$—X—, $R_2$—Y— and $R_3$, at least one piperidine radical of formula (II) be present.

Evans and Rasberger, U.S. Pat. No. 4,161,592 patented July 17, 1979, provide piperidine derivatives of 1,3-pyrimidine and 1,3,5-triazine which combine a light stabilizing effect and surprisingly good antioxidative properties in one and the same molecule. Moreover, the new compounds are distinguished by good color properites.

The compounds correspond to the general formula I

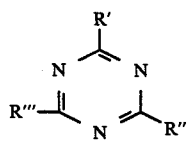

or to addition salts thereof, in which one of the radicals R', R" and R'" denotes a group of the formula II:

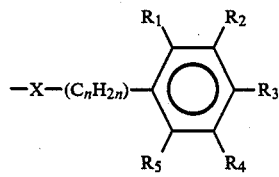

wherein one of $R_1$ and $R_3$ is —OH and the other is hydrogen, $R_2$ denotes $C_1$-$C_{12}$ alkyl, $C_5$-$C_7$ cycloalkyl, $C_6$-$C_{10}$ aryl or $C_7$-$C_9$ aralkyl, $R_4$ and $R_5$ are hydrogen, $C_1$-$C_{12}$ alkyl, $C_5$-$C_7$ cycloalkyl, $C_6$-$C_{10}$ aryl or $C_7$-$C_9$ aralkyl, n denotes 0 to 12 and X denotes —O—, —S— or —$NR_6$— wherein $R_6$ is hydrogen or $C_1$-$C_{12}$ alkyl, and one of the radicals R', R" and R'" denotes one of the groups

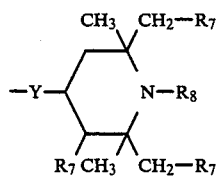

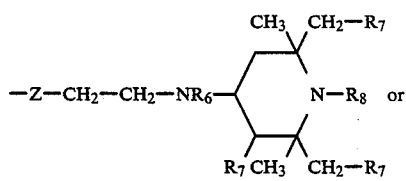

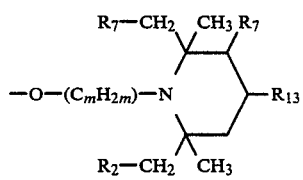

in which Y is —O— or —$NR_6$— wherein $R_6$ has the meaning defined above, Z denotes —O— or —S—, m is 1 to 6, $R_7$ is hydrogen or $C_1$-$C_8$ alkyl and $R_8$ is hydrogen, oxy, $C_1$-$C_{12}$ alkyl, $C_3$-$C_6$ alkenyl, $C_3$-$C_4$ alkinyl, $C_2$-$C_{21}$ alkoxyalkyl, $C_7$-$C_9$ aralkyl, 2,3-opoxypropyl, an aliphatic acyl group with 1-4 C atoms or one of the groups —$CH_2COOR_9$, —$CH_2$—$CH(R_{10})$—$OR_{11}$, —$COOR_{12}$ or —$CONHR_{12}$, wherein $R_9$ is $C_1$-$C_{12}$ alkyl, $C_{3l}$-$C_6$ alkenyl, phenyl, $C_7$-$C_8$ aralkyl or cyclohexyl, $R_{10}$ is hydrogen, methyl or phenyl, $R_{11}$ denotes hydrogen, an aliphatic, aromatic, araliphatic or alicyclic acyl group with 1-18 C atoms, wherein the aromatic part, if appropriate, can be substituted by chlorine, $C_1$-$C_4$ alkyl, $C_1$-$C_8$ alkoxy and/or by hydroxyl, and $R_{12}$ denotes $C_1$-$C_{12}$ alkyl, cyclohexyl, phenyl or benzyl, and $R_{13}$ denotes hydrogen, —OH or one of the groups —O—CO—$R_{14}$ or —$NR_{12}$—CO—$R_{14}$, wherein $R_{14}$ denotes $C_1$-$C_{12}$ alkyl or phenyl, and one of the radicals R', R" and R'" independently of the others denotes an identical or different group of the formula II, or denotes an identical or different group III, IV or V, or denotes —$N_3$ or one of the groups —S—$R_{15}$, —$OR_{17}$, —P(O)—$(OR_{17})_2$ or —$NR_{18}R_{19}$, wherein $R_{15}$ denotes hydrogen, $C_1$-$C_{18}$ alkyl, $C_5$-$C_7$ cycloalkyl, $C_6$-$C_{10}$ aryl, $C_7$-$C_9$aralkyl or the group —$(C_pH_{2p})$—CO—$OR_{16}$ wherein $R_{16}$ is $C_1$-$C_{18}$ alkyl and p denotes 1 to 6, $R_{17}$ denotes $C_1C_{18}$ alkyl, $C_6$–$C_{10}$ aryl or $C_7$–$C_9$ aralkyl and $R_{18}$ and $R_{19}$ independently of one another denote hydrogen, $C_1$–$C_{13}$ alkyl, $C_5$–$C_7$ cycloalkyl, $C_6$–$C_{10}$ aryl, $C_7$–$C_9$ aralkyl or the group

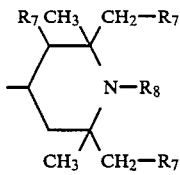 (VI)

in which $R_7$ and $R_8$ have the meaning defined above.

Rody and Berner, U.S. Pat. No. 4,234,728 patented Nov. 18, 1980, provide s-triazine derivatives which contain, as substituents in the 2-, 4- and 6-position, at least one polyalkylpiperidine radical and at least one N-methylolamino group, or the ethers thereof. These compounds can be mono- or polytriazines, and have the formula I or II

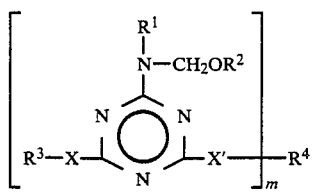 (I)

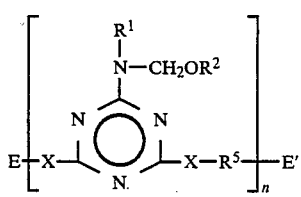 (II)

in which m is an integer from 1 to 4 and n is a value from 2 to 50, X and X' are —O—, —S— or —$NR^6$—, in which $R^6$ is hydrogen, $C_1$–$C_{18}$ alkyl, $C_3$–$C_8$ alkenyl, $C_1$–$C_4$ hydroxyalkyl, $C_2$–$C_{13}$ alkoxyalkyl, $C_5$–$C_{12}$ cycloalkyl, $C_6$–$C_{10}$ aryl, $C_7$–$C_9$ phenylalkyl or a polyalkyl piperidine group of the formula III

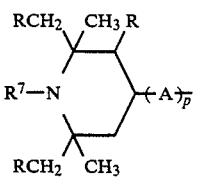 (III)

in which R is hydrogen or methyl, p is 0 or 1, A is $C_1$–$C_4$ alkylene, —$NR^6$—$C_2$—$C_{12}$ alkylene or —OCH$_2$CH$_2$CH$_2$— and R is H, O, $C_1$–$C_{12}$ alkyl, allyl, benzyl or a —CH$_2$CH($R^8$)—OH group, in which $R^8$ is H, CH$_3$, C$_2$H$_5$ or phenyl, and $R^1$ and $R^3$ are hydrogen, $C_1$–$C_{18}$ alkyl, $C_3$–$C_8$ alkenyl, $C_1$–$C_4$ hydroxyalkyl, $C_2$–$C_{13}$ alkoxyalkyl, $C_5$–$C_{12}$ cycloalkyl, $C_6$–$C_{10}$ aryl, $C_7$–$C_9$ phenylalkyl, phenyl or phenylalkyl which is substituted by 1 or 2 $C_1$–$C_8$ alkyl groups and/or OH and/or $C_1$–$C_4$ alkoxy, or a polyalkylpiperidine group of the formula III, $R^2$ is hydrogen, $C_1$–$C_{18}$ alkyl, $C_3$–$C_8$ alkenyl, $C_2$–$C_6$ hydroxyalkyl or $C_3$–$C_6$ alkoxylalkyl, $R^4$, if m is 1, is hydrogen, $C_1$–$C_{18}$ alkyl, $C_3$–$C_8$ alkenyl, $C_2$–$C_4$ hydroxyalkyl, $C_3$–$C_6$ alkoxyalkyl, $C_5$–$C_{10}$ aryl, $C_7$–$C_9$ phenylalkyl, phenyl or phenylalkyl which is substituted by 1 or 2 $C_1$–$C_8$ alkyl groups and/or OH and/or $C_1$–$C_4$ alkoxy, or a polyalkylpiperidine group of the formula III, and if m is 2 is $C_2$–$C_{12}$ alkylene or oxaalkylene, $C_4$–$C_{12}$ *alkenylene*, $C_6$–$C_{10}$ arylene, a phenlene-Z-phenylene-radical, in which Z is —O—, —S—, —SO$_2$—, —CH$_2$— or —C(CH$_3$)$_2$— or a radical of the formula —(CH$_2$)$_r$—NY$\{$(CH$_2$)$_r$—NY$\}_q$(CH$_2$)$_r$—, wherein r is 2 or 3 and q is 0 or 1 and Y is a triazinyl group of the formula IV,

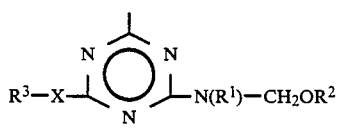 (IV)

and if m is 3 is a $R^3$—C(CH$_2$—)$_3$ radical, in which $R^3$ is $C_1$–$C_4$alkyl, and if m is 4 is a C(CH$_2$—)$_4$ radical, $R^5$ is $C_2C_{12}$ alkylene and E and E' are corresponding end groups and at least one of the radicals $R^1$, $R^3$, $R^4$ or $R^5$ is a piperidine radical of the formula III.

Cassandrini and Tozzi, U.S. Pat. No. 4,263,434 patented Apr. 21, 1981, provides piperidyltriazine derivatives which are useful for improving the stability to light, heat and oxidation of polymeric substances, and which have the general formula (I):

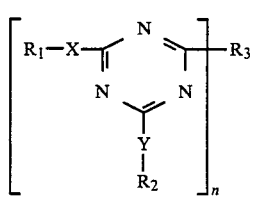 (I)

wherein $R_1$, $R_2$ same or different are hydrogen, hydroxyl, a straight or branched chain $C_1$ to $C_{18}$ alkyl, a $C_5$ to $C_{18}$ cycloalkyl, a substituted or not substituted $C_6$ to $C_{18}$ aryl, a $C_7$ to $C_{18}$ aralkyl, or a piperidine radical of formula (II)

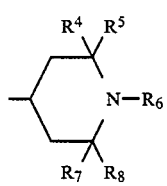 (II)

in which $R_4$, $R_5$, $R_7$, $R_8$ same or different, are each a $C_1$ to $C_6$ alkyl and $R_6$ is H, O, a $C_1$ to $C_{12}$ alkyl, a $C_2$ to $C_{12}$ alkenyl or alkinyl;

$R_1$, $R_2$ can also represent a group

in which $R_9$, $R_{10}$ same or different, are each hydrogen, $C_1$ to $C_8$ alkyl, $C_5$ to $C_8$ cycloalkyl or $C_6$ to $C_8$ aryl;

X, Y same or different represent —O—, —S—,

$R_{11}$ being H, a straight or branched chain $C_1$ to $C_{18}$ alkyl, $C_5$ to $C_{18}$ *cycloalkyl*, $C_6$ to $C_{18}$ aryl, $C_7$ to $C_{18}$ aralkyl, or a piperidine radical of formula (II).

The radicals $R_1$—X—, $R_2$—Y—, taken as a single substituent group, can also be radicals from nitrogenous heterocyclic compounds having 5 to 8 members, linked to the triazine ring by a bisubstituted nitrogen atom of said radical.

They can also represent Cl— or Br—;

n is an integer from 2 to 6;

$R_3$ is a n-valent residue deriving from a polyalcohol, a polymercaptan or a polyamine by reaction of the active H atoms thereof with a halogen atom of a monohalogen triazine;

$R_3$ can be a radical of type $R_{12}$—$(Z)_n$—, wherein $R_{12}$ is a n-valent, $C_1$ to $C_{18}$ aliphatic, $C_5$ to $C_{18}$ cycloaliphatic or $C_6$ to $C_{13}$ aromatic radical, and Z is —O—, —S—,

wherein $R_{11}$ has the same meaning as previously indicated.

When n=2, the radical $R_3$ can also be the bivalent radical of a nitrogenous heterocyclic compound having 6 to 8 members, the bisubstituted nitrogen atoms of which are linked to a triazine ring; when n=2, $R_3$ can also be a radical type

in which $R_{13}$, $R_{14}$, same or different, are each hydrogen, $C_1$ to $C_{12}$ alkyl, $C_5$ to $C_{12}$ cycloalkyl, $C_6$ to $C_{12}$ aryl; $C_7$ to $C_{12}$ aralkyl or a piperidine radical of formula (II).

When n=3, 4, 5, 6, $R_3$ can also be a radical of type

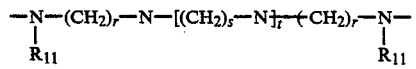

in which $R_{11}$ has the same meaning as previously indicated; r, s, same or different, are an integer from 2 to 6 and t is an integer from 0 to 3.

In formula (I) there is the condition that at least in one of the radicals $R_1$—X—, $R_2$—Y— and $R_3$, at least one piperidine radical of formula (II) be present.

Rody, U.S. Pat. No. 4,288,593, patented Sept. 8, 1981, provides polyalkylpiperidine derivatives of s-triazines of the formula

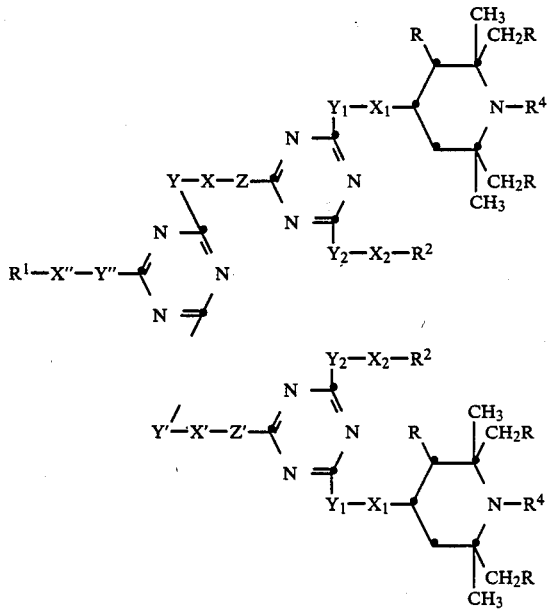

in which X and X' are a divalent organic radical, X", $X_1$ AND $X_2$ are a direct bond or a divalent organic radical, Y, Y', Y", $Y_1$, $Y_2$, Z and Z' are —O—, —S—, —NH— or —NR$^3$—, R is H or $CH_3$ and $R^1$, $R^2$ and $R^3$ are a monovalent organic radical or a polyalkylpiperidine group, or the group $R^1$—X"—Y"— is chlorine, and $R_4$ is H, O, alkyl, allyl or benzyl. These are stabilizers for polymeric materials, in particular to protect them against photochemical degradation.

Nikles, U.S. Pat. No. 4,315,859 patented Feb. 16, 1982, provides polymeric polyamine-1,3,5-triazines which have an excellent stabilizing action, of the general formula I

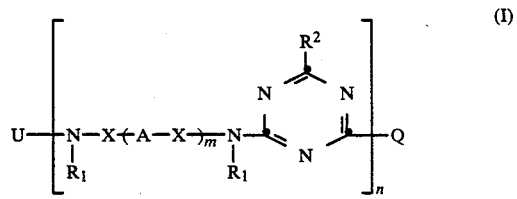

wherein the symbols which may or may not recur in the compound, and which on each possible recurrence can be the same or different, are defined as follows: X is $C_2$-$C_6$ alkylene, A is —O—, —S— or —NR—, wherein R, which is also recurring or non-recurring and on each possible recurrence can be the same or different, is hydrogen, $C_3$-$C_{12}$ cycloalkyl, $C_7$-$C_{18}$ aralkyl, $C_6$-$C_{10}$ aryl or the radical of the formula II

wherein $R^3$ is hydrogen, $C_1$-$C_{18}$ alkyl, $C_3$-$C_{12}$ alkenyl, $C_3$-$C_5$ alkynyl, $C_3$-$C_{18}$ alkoxyalkyl, $C_2$-$C_4$ hydroxyalkyl which is unsubstituted or substituted by phenyl or phenoxy, or $C_7$-$C_{18}$ aralkyl, and $R^4$ is hydrogen or methyl, or R is also one or more of the structural units contained with the brackets of formula I, said structural unit or units being terminally saturated by U and being bound through a triazine C atom, and wherein R and $R^1$ as end groups, each independently of the other, can be hydrogen, $C_1$-$C_{23}$ alkyl which can be interrupted by oxygen, $C_3$-$C_{12}$ cycloalkyl, $C_7$-$C_{13}$ aralkyl, $C_6$-$C_{10}$ aryl or the radical of the formula II, and $R^1$ as end group can also in addition be a group of the formula III

  (III)

wherein $R^5$ and $R^6$, each independently of the other, are U, $C_1$-$C_{23}$ alkyl which can be interrupted by oxygen, $C_3$-$C_{12}$ cycloalkyl, $C_7$-$C_{18}$ aralkyl, $C_6$-$C_{10}$ aryl, the radical of the formula II or a group of the formula IV

  (IV)

$R^2$ is halogen cyano, azido, hydrazido, phenyl, —$OR^7$, —$SR^7$ or '$NR^8R^{8'}$, wherein $R^7$ is hydrogen, $C_1$-$C_{18}$ alkyl, $C_3$-$C_{12}$ alkenyl, $C_3$-$C_{13}$ alkoxyalkyl, $C_3$-$C_{12}$ cycloalkyl, $C_7$-$C_{18}$ aralkyl, $C_6$-$C_{10}$ aryl, or the radical of the formula II, and $R^6$ and $R^{8'}$, each independently of the other, are hydrogen, $C_1$-$C_{23}$ alkyl which can be interrupted by oxygen, $C_3$-$C_{18}$ alkenyl, $C_3$-$C_5$ alkynyl, $C_2$-$C_{10}$ hydroxyalkyl, $C_2$-$C_5$ cyanoalkyl, $C_3$-$C_{12}$ cycloalkyl, $C_7$-$C_{18}$ aralkyl, $C_6$-$C_{10}$ aryl or the radical of the formula II, or $R^8$ and $R^{8'}$ together with the nitrogen atom to which they are attached form a pyrrolidine ring or a piperidine, morpholine or hexamethyleneimine ring which is unsubstituted or substituted by $C_1$-$C_4$ alkyl, or $R^2$ on each of its possible recurrences can also be a radical of the formula V

  (V)

wherein a can be 0, 1, 2, 3 or 4, or a radical of the formula VI

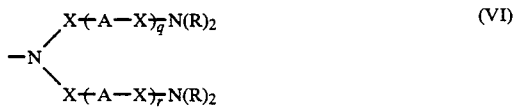  (VI)

wherein q can be 0, 1 and 2 and r can be 0, 1, 2 or 3, whilst the sum of r+q may not be more than 3, or $R^2$ can also be one or more of the structural units contained with the brackets of formula I, said structural unit or units being terminally saturated by Q and being bound through the amine nitrogen atom, and wherein $R^2$ as end group is halogen, phenyl, —$OR^7$, —$SR^7$, —$NR^8R^{8'}$, a group of the formula VII,

  (VII)

or of the formula VIII

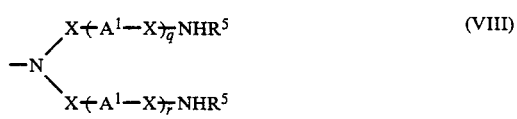  (VIII)

wherein $A^1$ is —O—, —S— or —$NR^5$, whilst Q is halogen, —$NR^8R^{8'}$, —OH, —OMe/b, wherein Me/b represents an alkali metal or alkaline earth metal of the valency b, and b is 1 or 2, or Q is a radical of the formula VII or VIII, U is hydrogen, a group of the formula

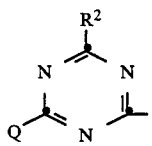

or $C_1$-$C_{24}$ acyl, and n can be an integer from 1 to 100, with the priviso that at least one R, one $R^1$ or one $R^2$ is or contains a group of the formula II and, if m is 0, at least one $R^1$ must be a group of the formula III or IV.

Rody, U.S. Pat. No. 4,294,963, patented Oct. 13, 1981, provides polyalkylpiperidine derivatives of s-triazines as stabilizers for polymers. The compounds have the formula I or II

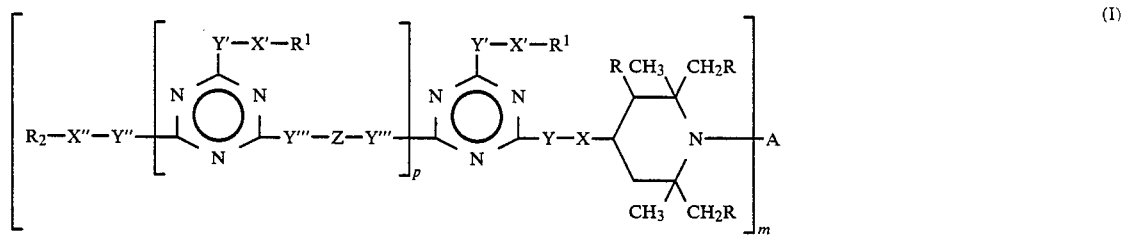  (I)

-continued $$\text{E}-\left[\begin{array}{c}\text{RCH}_2\quad\text{CH}_3\;\text{R}\\ \text{N}\\ \text{RCH}_2\quad\text{CH}_3\end{array}-X''-Y_2\right]\left[\begin{array}{c}Y'-X'-R^1\\ N\quad N\\ N\end{array}Y'''-Z-Y''''\right]_p\left[\begin{array}{c}Y'-X'-R^1\\ N\quad N\\ N\end{array}Y-X\begin{array}{c}\text{R}\;\text{CH}_3\quad\text{CH}_2\text{R}\\ \text{N}-\text{B}\\ \text{CH}_3\quad\text{CH}_2\text{R}\end{array}\right]_n-\text{E}' \qquad (II)$$

wherein m is 2, 3 or 4, n is 2 to 50, p is 0 or 1, X, X' and X" represent a direct bond, $C_1$-$C_4$ alkylene or —OCH$_2$CH$_2$CH$_2$—, the O of which is not bonded to Y, Y' or Y'''; Y, Y', Y''' and Y'''' represent —O—, —S—, —NH— or —NR$^3$—, Z represents $C_2$-$C_{12}$ alkylene; $C_4$-$C_{20}$ alkylene interrupted by —O—, —S—, —NH— or —NR$^3$—, xylylene, $C_6$-$C_{12}$ arylene or phenylene Q' phenylene, wherein Q' is —CH$_2$—, >C(CH$_3$)$_2$, —SO$_2$— or —O—, R represents hydrogen or $C_1$-$C_4$ alkyl, R$^1$, R$^2$ and R$^3$ represent $C_1$-$C_{12}$ alkyl, $C_2$-$C_8$ alkoxyalkyl, $C_2$-$C_4$ hydroxyalkyl, $C_5$-$C_{12}$ cycloalkyl, $C_7$-$C_{12}$ aralkyl, $C_3$-$C_{18}$ alkenyl, $C_6$-$C_{10}$ aryl, phenyl which is substituted by one or two $C_1$-$C_8$ alkyl groups and/or by OH and/or by $C_1$-$C_4$ alkoxy, or represent a polyalkylpiperidinyl group of the formula III $$\text{R}^4-\text{N}\begin{array}{c}\text{RCH}_2\quad\text{CH}_3\\ \quad\text{R}\\ \text{RCH}_2\quad\text{CH}_3\end{array} \qquad (III)$$

or, if Y' or Y" is —NR$^3$— and X' or X" is a direct bond, R$^1$ and R$^2$ together with the nitrogen atom form a pyrrolidone, piperidine or morpholine ring, R$^4$ represents hydrogen, O, $C_1$-$C_{12}$ alkyl, allyl or benzyl, A if m is 2, represents $C_2$-$C_{12}$ alkylene, $C_4$-$C_8$ alkenylene, xylylene or a radical of the formula —CH$_2$—C≡C—CH$_2$—, —CH$_2$—⟨biphenyl⟩—CH$_2$—,

—CH$_2$—⟨C$_6$H$_4$⟩—O—⟨C$_6$H$_4$⟩—CH$_2$—,

—CH$_2$—COO—R$^5$—OOC—CH$_2$, —CH$_2$—CH(OH)—CH$_2$— or —CH$_2$CH(OH)CH$_2$—D—CH$_2$CH(OH)CH$_2$—, or if m is 3, represents a group of the formula $$-\text{CH}_2\text{CH(OH)CH}_2-\text{T}\begin{array}{c}\text{CH}_2\text{CH(OH)CH}_2-\\ \text{CH}_2\text{CH(OH)CH}_2-\end{array}$$

and, if m is 4, represents a group of the formula $$\begin{array}{c}-\text{CH}_2\text{CH(OH)CH}_2\\ -\text{CH}_2\text{CH(OH)CH}_2\end{array}\text{Q}\begin{array}{c}\text{CH}_2\text{CH(OH)CH}_2-\\ \text{CH}_2\text{CH(OH)CH}_2-\end{array}$$

B represents $C_2$-$C_{12}$ alkylene, $C_4$-$C_8$ alkenylene, xylylene or a radical of the formula —CH$_2$—COO—R$^5$—OOC—CH$_2$, —CH$_2$—CH(OH)—CH$_2$ or —CH$_2$CH(OH)CH$_2$—D—CH$_2$CH(OH)CH$_2$, R$^5$ represents $C_2$-$C_8$ alkylene, $C_4$-$C_8$ oxaalkylene or cyclohexylene, D represents a divalent radical of the formula —O—R$^6$—O—, —O—C(O)—R$^7$—C(O)—O—, —OCH(R$^8$)CH$_2$O—R$^6$—OCH$_2$CH(R$^8$)O— or $$\begin{array}{c}\text{R}^9\;\;\;\;\text{R}^9\\ -\text{N}\quad\quad\text{N}-\text{CH}_2\text{CH}_2\text{O}-\\ \quad\quad\text{O}\end{array}\quad\text{or}$$

$$\begin{array}{cc}\text{R}^9\quad\text{R}^9 & \text{R}^9\quad\text{R}^9\\ -\text{N}\quad\text{N}-\text{CH}_2-\text{N}\quad\text{N}-\\ \;\;\;\text{O}\quad\quad\quad\quad\quad\text{O}\end{array}$$

R$^6$ represents $C_2$-$C_{12}$ alkylene, $C_6$-$C_{12}$ cycloalkylene, $C_6$-$C_{12}$ arylene or phenylene Z$_1$ phenylene, wherein Z$_1$ represents —CH$_2$—, >C(CH$_3$)$_2$, —SO$_2$— or —O—, R$^7$ represents a direct bond, $C_1$-$C_{12}$ alkylene, $C_2$-$C_6$ alkenylene, $C_6$-$C_{12}$ cycloalkylene or cycloalkenylene or $C_6$-$C_{12}$ arylene, R$^8$ and R$^9$ are hydrogen or $C_1$-$C_4$ alkyl, T represents a trivalent radical of the formulae $$-\text{O}-\text{R}^{10}-\text{O}-,\quad -\text{N}\begin{array}{c}\text{O}\\ \|\\ \text{N}-\\ \|\\ \text{O}\end{array}\text{N}-,$$

—OCH$_2$CH$_2$CO—N⟨piperazine⟩N—COCH$_2$CH$_2$O— or

⟨with COCH$_2$CH$_2$O—⟩

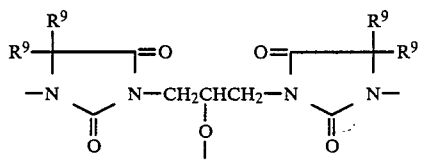

R¹⁰ represents a trivalent aliphatic hydrocarbon radical of 3 to 10 carbon atoms, Q represents a quadrivalent radical of the formula

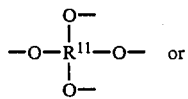

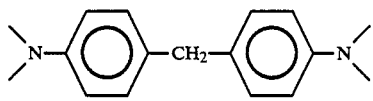

R¹¹ represents a quadrivalent aliphatic hydrocarbon radical of 4 to 10 carbon atoms, and E and E' represent end groups.

Sankyo and Ciba-Geigy British Pat. No. 1,496,454 discloses 3- or 5-substituted 2,2,6,6-tetra-4-piperidinol derivatives of the general formula:

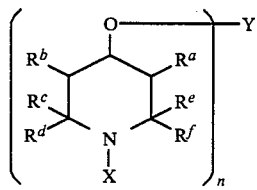

In this formula, $R^a$ and $R^b$ may be hydrogen, but one must be lower alkyl, alkenyl or alkynyl, so that a 3- or 5-substituent is necessary.

Y is a mono to tetravalent organic group, and X can be hydrogen.

Various types of Y groups are illustrated at page 6, column 1, including a group of formula

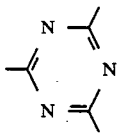

which is 1,3,5-triazine.

The Sankyo British patent also indicates in the summary of prior art at page 2, column 1, that German Offenlegungsschrift No. 2,319,816 discloses 2,4,6-tri(-piperidyl-4-oxy-1,3,5-triazine derivatives.

Rasberger and Karrer, U.S. Pat. No. 4,317,911, patented Mar. 2, 1982, discloses piperidinyl isocyanurates having the general formula:

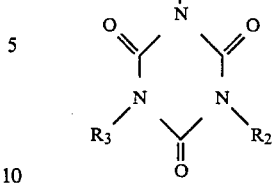

and to addition salts thereof, in which $R_1$ denotes

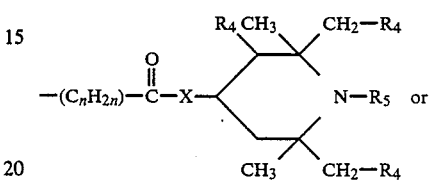

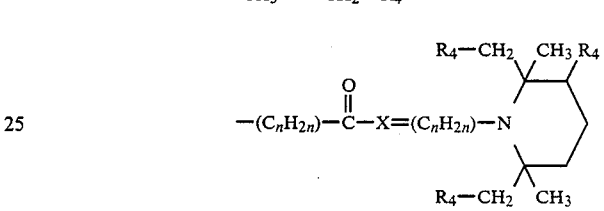

These compounds have the piperidinyl group attached to the isocyanurate nucleus by way of a

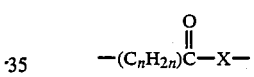

linking group, where X can be oxygen.

Morimura, Toda and Kurumada, U.S. Pat. No. 4,321,374 patented Mar. 23, 1982, provides s-triazine derivatives having the formula

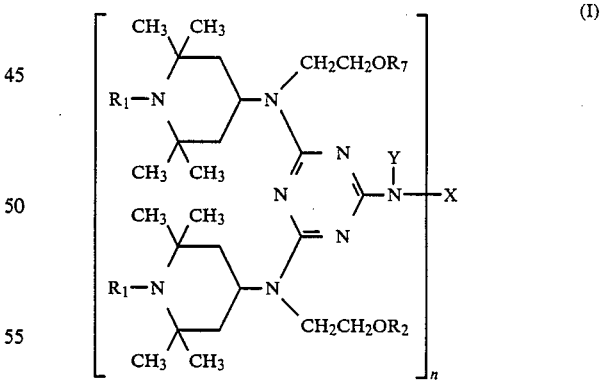

(I)

wherein $R_1$ represents hydrogen atom or methyl group, $R_2$ represents hydrogen atom, an alkanoyl group having from 2 to 18 carbon atoms or 3-(3,5-di-tert-butyl-4-hydroxyphenyl) propionyl group, n is 1 or 2, when n is 1, X represents an alkyl group having from 1 to 18 carbon atoms, benzyl group or a group of the formula —$CH_2CH_2OR_2$ (wherein $R_2$ is as defined above) and Y represents hydrogen atom, a group of the formula

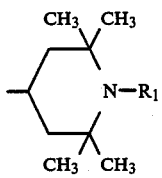 (II)

or a group of the formula

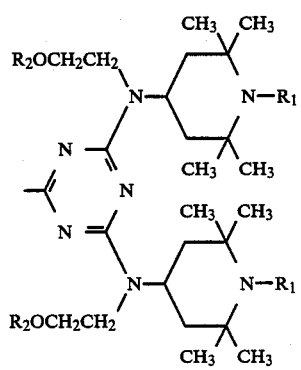 (III)

(wherein $R_1$ and $R_2$ are as defined above),
when n is 2,
X represents an alkylene group having from 2 to 6 carbon atoms, xylylene group or a group of the formula

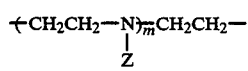

(wherein m is an integer from 1 to 4 and Z represents a group of the above formula (III)) and
Y represents hydrogen atom or a group of the above formula (II).

In the formula (I), $R_2$ as an alkanoyl group having from 2 to 18 carbon atoms can be, for example, acetyl, propionyl, butyryl, hexanoyl, octanoyl, lauroyl, palmitoyl or stearoyl, in particular, it is desirably an alkanoyl group having from 2 to 4 carbon atoms. X as an alkyl group having from 1 to 18 carbon atoms can be a straight or branched chain alkyl, for example, methyl, ethyl, propyl, isopropyl, butyl, isobutyl, tert-butyl, hexyl, octyl, 2-ethylhexyl, tert-octyl, decyl, dodecyl, tetradecyl or octadecyl, in particular, it is desirably an alkyl group having from 8 to 18 carbon atoms. X as an alkylene group having from 2 to 6 carbon atoms can be, for example, 1,2-ethylene, 1,2-propylene, 1,4-butylene or 1,6-hexylene, desirably 1,6-hexylene.

Preferred compounds of the formula (I) are those in which $R_1$ is hydrogen atom or $R_2$ is hydrogen atom.

More preferred compounds of the formula (I) are those in which (1) $R_1$ and $R_2$ are hydrogen atom, n is 1, X is an alkyl group having from 8 to 10 carbon atoms and Y is hydrogen atom or 2,4-bis[2-hydroxy-N-(2,2,6,6-tetramethyl-4-piperidyl)ethylamino]-1,3,5-triazine-6-yl group;

(2) $R_1$ and $R_2$ are hydrogen atom, n is 1, X is 2-hydroxyethyl group and Y is 2,2,6,6-tetramethyl-4-piperidyl group;

(3) $R_1$ and $R_2$ are hydrogen atom, n is 2, X is 1,6-hexylene group or a group of the formula

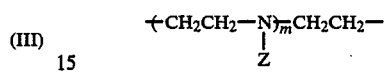

(wherein m is an integer from 1 to 4 and Z is 2,4-bis[2-hydroxy-N-(2,2,6,6-tetramethyl-4-piperidyl)ethylamino]-1,3,5-triazine-6-yl group) and Y is hydrogen atom.

U.K. Patent Application No. 2,117,377 published Oct. 12, 1983 discloses piperidine derivatives that have the general formula

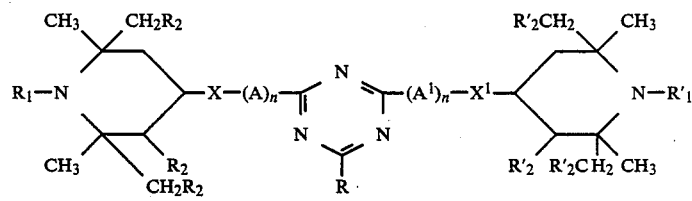

where
R denotes hydrogen, alkyl, cycloalkyl, alkenyl, aralkyl or aryl;
$R_1$ and $R'_1$ denote hydrogen, alkyl, alkenyl, or aralkyl;
$R_2$ and $R'_2$ denote hydrogen or methyl;
X and X' denote oxygen or $NR_3$;
$R_3$ denotes hydrogen, alkyl, cycloalkyl or aralkyl;
A and A' denote $(CH_2)_mX''$;
m equals 2 or 3;
X'' has the same meaning as X and X', and
n can be 0 or 1.
These are used as stabilizers for polymers.

U.S. Pat. No. 4,500,663, patented Feb. 19, 1985, provides N,N,N-tris(2,2,6,6-tetramethyl-4-piperidone ketal)-1,3,5-triazines having the formula:

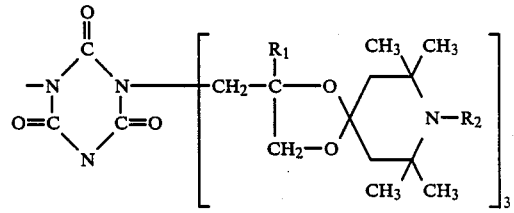

wherein:
$R_1$ is selected from the group consisting of hydrogen and alkyl having from one to about four carbon atoms; and
$R_2$ is selected from the group consisting of hydrogen; oxyl O; alkyl, hydroxy alkyl and epoxyalkyl having from one to about eighteen carbon atoms; acyl having from one to about eighteen carbon atoms; cycloalkyl having from three to about eighteen carbon atoms; phenyl; phenalkyl and alkylphenyl having from seven to about twenty-four carbon atoms; as well as synthetic resin compositions having an improved resistance to deterioration and containing such compounds.

U.S. Pat. No. 4,540,728, patented Sept. 10, 1985, provides polymers of diallyl-1,3,5-triazino-4-(2,2,6,6-tetramethyl piperidyl) amines having a molecular weight within the range from about 800 to about 20,000, and derived from the monomer:

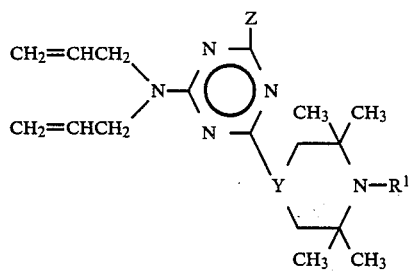

wherein:

$R_1$ is selected from the group consisting of hydrogen; oxyl; alkyl and hydroxyalkyl having from one to about eighteen carbon atoms; alkyaryl having from seven to about eighteen carbon atoms; epoxy alkyl having from three to about eighteen carbon atoms; and acyl having from two to about eighteen carbon atoms;

Y is selected from the group consisting of

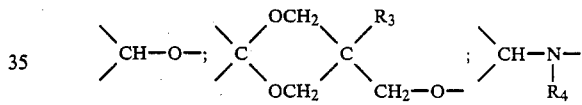

where $R_2$ and $R_3$ are hydrogen or alkyl having from one to about eight carbon atoms and n is 0 or 1;

Z is selected from the group consisting of

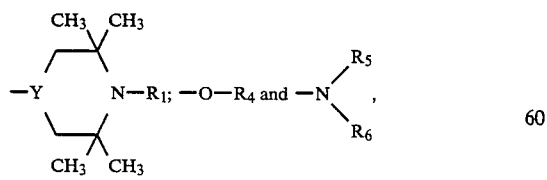

in which $R_4$, $R_5$ and $R_6$ are selected from the group consisting of hydrogen; alkyl having from one to about eighteen carbon atoms; cycloalkyl having from three to about twelve carbon atoms; and aryl having from six to about thirty carbon atoms; as well as stabilized synthetic resin compositions having an improved resistance to deterioration by light and containing such a polymer.

U.S. Pat. No. 4,491,643, patented Jan. 1, 1985, provides bis(2,2,6,6-tetramethylpiperidyl-1,3,5-triazinyl)-spirodiamines and spiroglycol ethers having the formula:

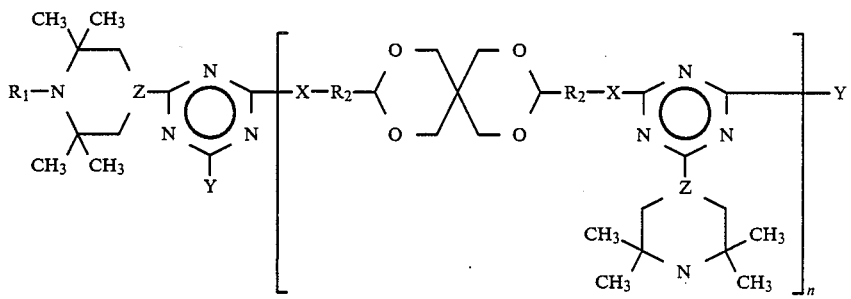

wherein:

$R_1$ is selected from the group consisting of hydrogen, alkyl having from one to about eighteen carbon atoms, hydroxyalkyl having from two to about six carbon atoms; epoxyalkyl having from three to about eight carbon atoms; alkylaryl having from seven to about eighteen carbon atoms; acyl having from two to about eight carbon atoms; and oxyl;

$R_2$ is alkylene having from one to about six carbon atoms;

Z is selected from the group consisting of

in which $R_3$ is alkyl having from one to about six carbon atoms; and $R_4$ is selected from the group consisting of hydrogen; alkyl having from one to eighteen carbon atoms; cycloalkyl having from about four to about eight carbon atoms; hydroxy alkyl and alkoxyalkyl having from two to about twelve carbon atoms and dialkylamino having from two to about ten carbon atoms;

X is selected from the group consisting of —O— and $$-\underset{\underset{R_5}{|}}{N}-$$

in which $R_5$ is selected from the group consisting of hydrogen, alkyl having from one to about eighteen carbon atoms; cycloalkyl having from about four to about eight carbon atoms; hydroxy alkyl and alkoxyalkyl having from two to about twelve carbon atoms, and dialkylamino having from two to about ten carbon atoms; and

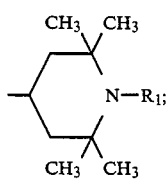

Y is selected from the group consisting of:

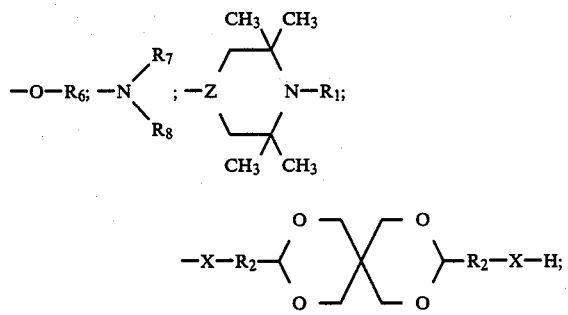

and Cl; in which R₆ is selected from the group consisting of alkyl having from one to about eighteen carbon atoms; cycloalkyl having from about four to about eight carbon atoms; hydroxy alkyl and alkoxyalkyl having from two to about twelve carbon atoms and dialkylamino having from two to about ten carbon atoms and aryl and alkaryl having from six to about twenty-four carbon atoms;

R₇ and R₈ are selected from the group consisting of hydrogen, alkyl having from one to about eighteen carbon atoms; and alkylene forming a heterocyclic ring including the nitrogen atom in the ring and having from four to seven carbon atoms and no or one oxygen atom; and n is a number from 1 to about 50 representing the average number of units enclosed by the brackets; and synthetic resin compositions containing the same as light stabilizers.

Additional patents disclosing such compounds include Rody U.S. Pat. No. 4,288,593, Morimura et al U.S. Pat. No. 4,322,527 and Japan Kokai No. 67749/78 and 102637/80.

The Cassandrini et al compounds having more than 2 triazine rings derived from polyamines or polyols have an exceptionally good heat stability and low extractability, but the stabilizing effect of these compounds is not fully satisfactory.

In accordance with the present invention, poly(2,2,6,6-tetramethyl-piperidylamino-1,3,5-triazines) are provided having the formula:

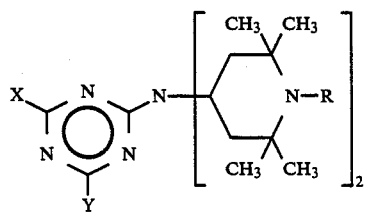     I in which:

R is selected from the group consisting of hydrogen; alkyl, alkenyl, cycloalkyl, hydroxyalkyl and alkoxy having from one to about twelve carbon atoms; acyl having from about one to about twelve carbon atoms; and oxyl;

X and Y are each selected from the group consisting of

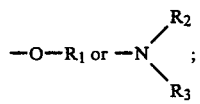

wherein:

R₁ is selected from the group consisting of alkyl, hydroxyalkyl and alkylenealkoxy having from one to about twelve carbon atoms; cycloalkyl having from three to about twelve carbon atoms; and aryl having from six to about eighteen carbon atoms;

R₂ and R₃ are selected from the group consisting of hydrogen; alkyl having from one to about twelve carbon atoms; cycloalkyl having from three to about twelve carbon atoms; and aryl having from six to about eighteen carbon atoms; and R₂ and R₃ taken together as a five to six member ring including the nitrogen atom in the ring; and

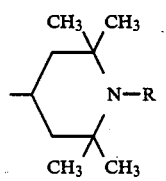

These compounds have an improved stabilizing effectiveness, as compared to previous compounds of this type, and impart to synthetic polymer compositions a considerably improved resistance to deterioration upon exposure to ultraviolet light.

Exemplary R₁, R₂ and R₃ alkyl include methyl, ethyl, propyl, isopropyl, butyl, isobutyl, tertiary-butyl, secondary-butyl, amyl, isoamyl, secondary-amyl, tertiary-amyl, hexyl, isohexyl, tertiary-hexyl, heptyl, isoheptyl, secondary-heptyl, octyl, isooctyl, 2-ethylhexyl, nonyl, isononyl, decyl, isodecyl, dodecyl, isododecyl, hexadecyl and octadecyl.

Exemplary R₁ hydroxyalkyl include 2-hydroxyethyl, 2-hydroxypropyl, 4-hydroxybutyl, 2,3-dihydroxybutyl, 6-hydroxy-hexyl, 12-hydroxy-dodecyl.

Exemplary R₁ alkoxy include methoxy, ethoxy, propoxy, butoxy, amyloxy, hexoxy, heptoxyl, decoxy, dodecoxy, methoxyethyl, butoxyethyl, 2,3-epoxypropyl, ethoxydecyl, and propoxypropyl.

Exemplary R₁ alkenyl include allyl, butenyl, pentenyl, hexenyl, heptenyl, octenyl, decenyl, and dodecenyl.

Exemplary R₁ acyl include acetyl, propionyl, butyroyl, acryloyl, methacryloyl, octanoyl and benzoyl.

Exemplary R₁ cycloalkyl include cyclopropyl, cyclobutyl, cyclopentyl, cyclohexyl, cycloheptyl, cyclooctyl and cyclododecyl.

Exemplary R₁, R₂ and R₃ aryl include phenyl, naphthyl, tolyl, xylyl, mesityl, tertiary-butylphenyl, octylphenyl, 2,4-di-tertiary-butylphenyl, nonylphenyl and dinonylphenyl.

Exemplary five- and six-member rings formed with R₂, R₃ and the nitrogen atom include pyrollidino, piperidino, morpholino and methylpiperidino.

Exemplary X and Y alkylamino include dimethyl amino, diethylamino, methyl cyclohexylamino, dipropylamino, and dicyclohexyl amino.

The following compounds are exemplary:

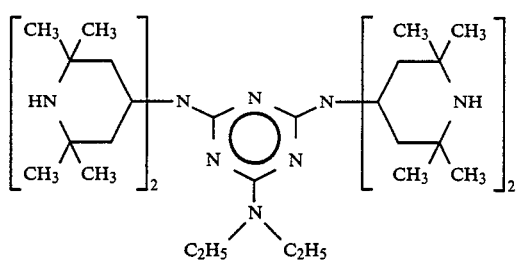
1.
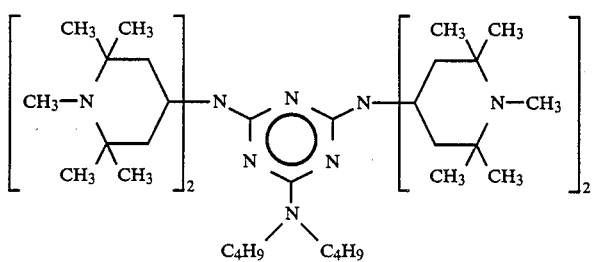
2.
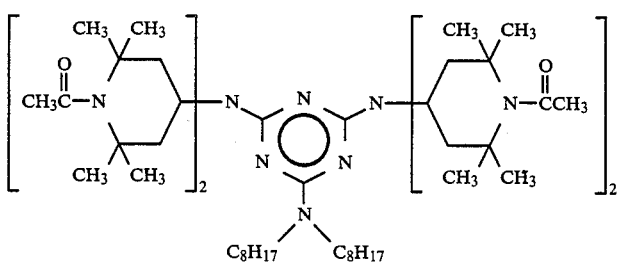
3.
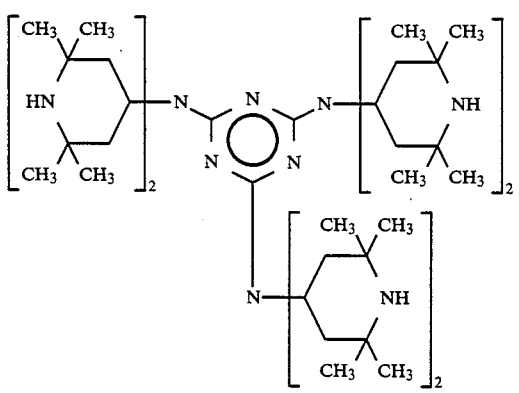
4.
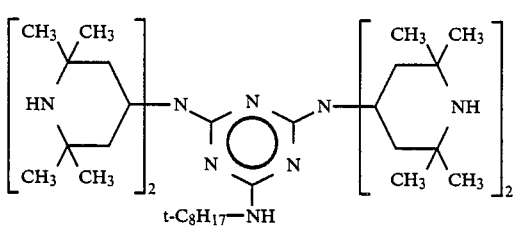
5.

6.
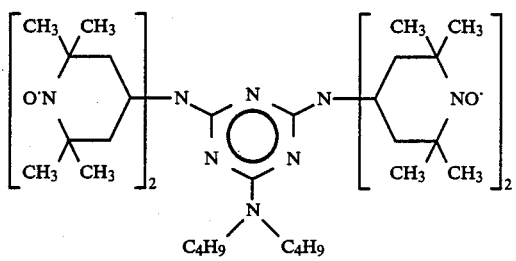
7.
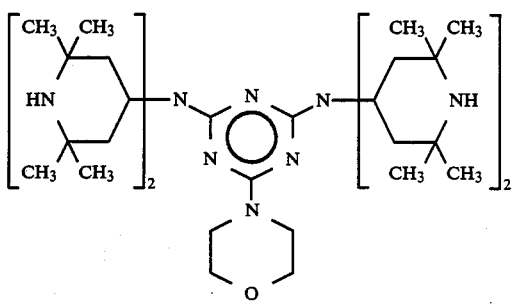
8.
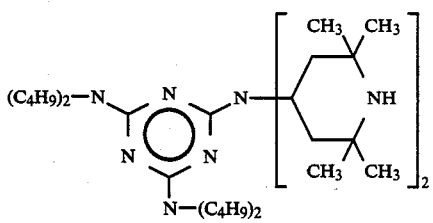
9.
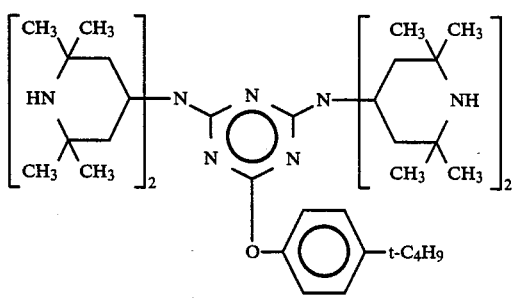
10.
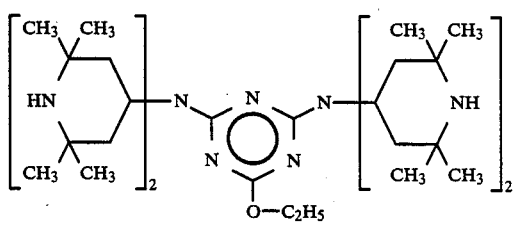
11.
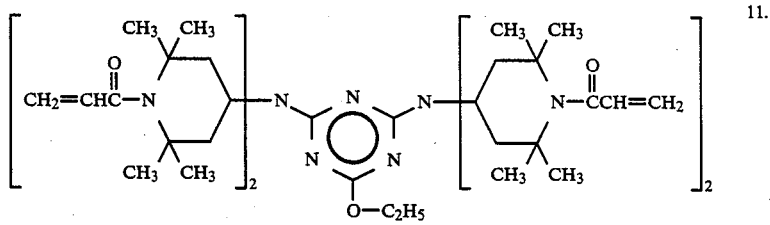

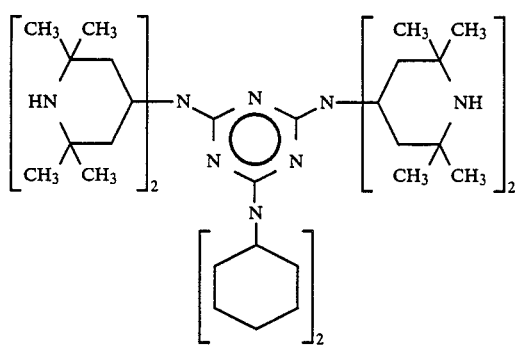
12.
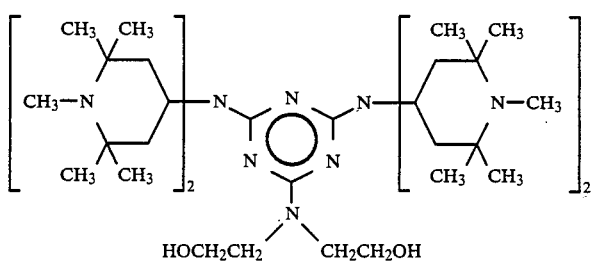
13.
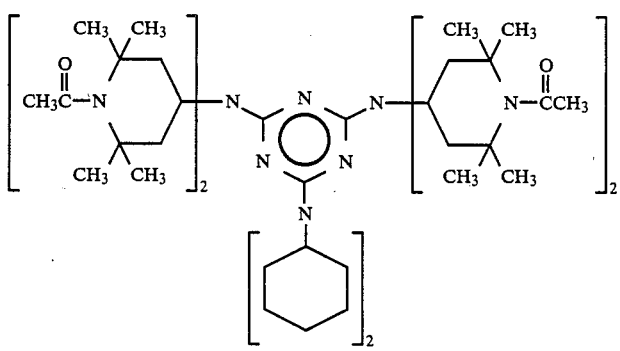
14.
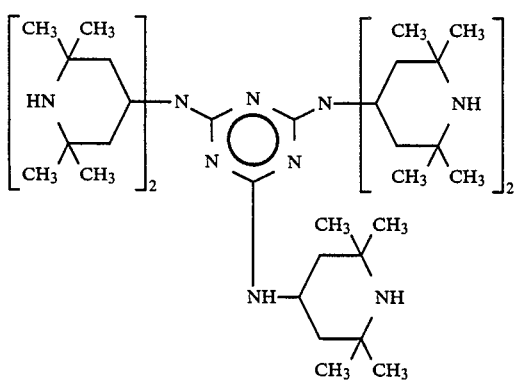
15.
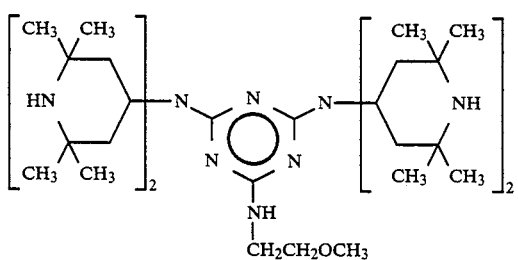
16.

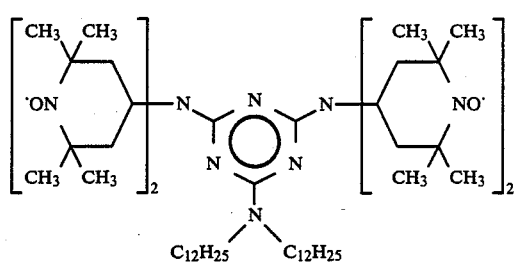
17.
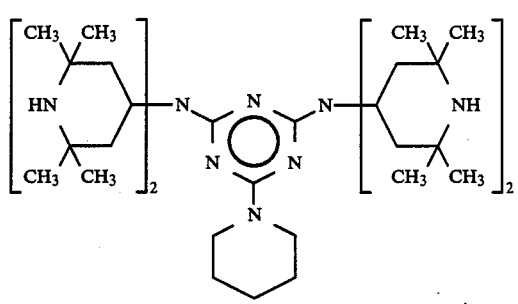
18.
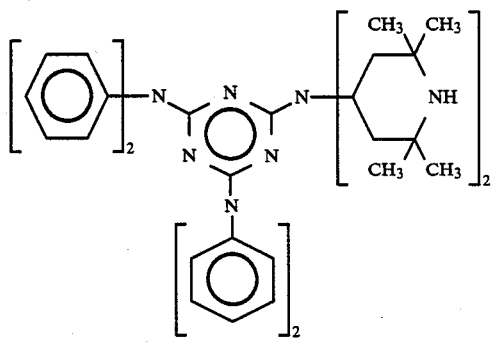
19.
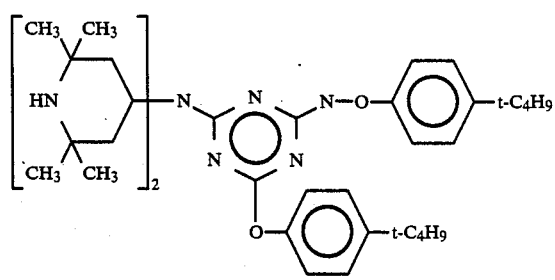
20.
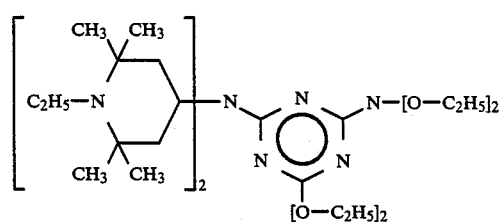
21.

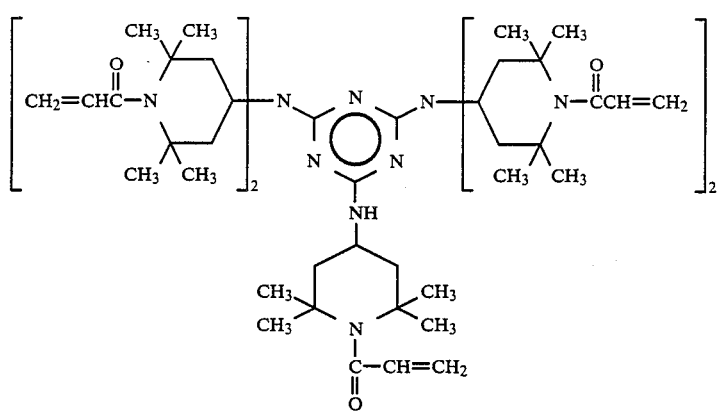
22.
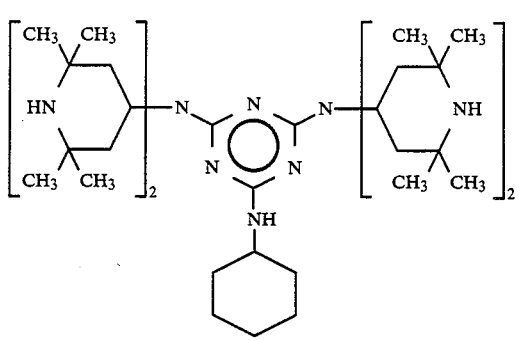
23.
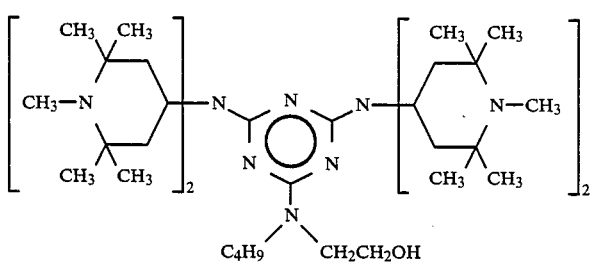
24.
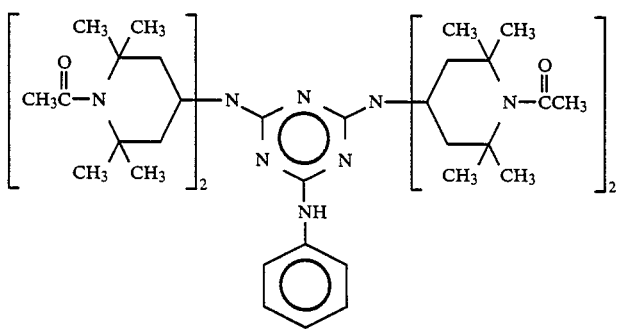
25.

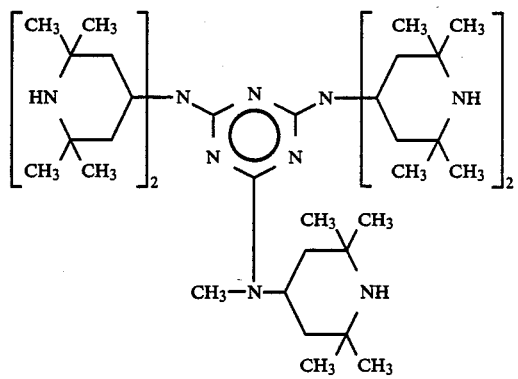
26.
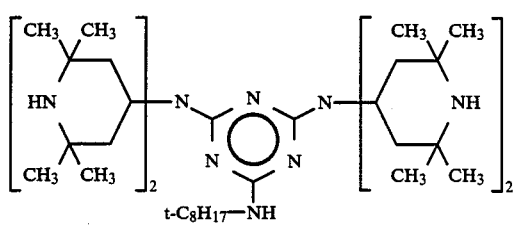
27.
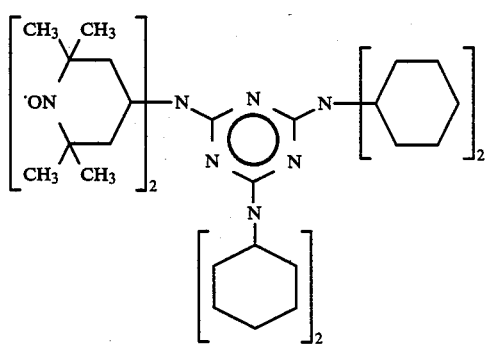
28.
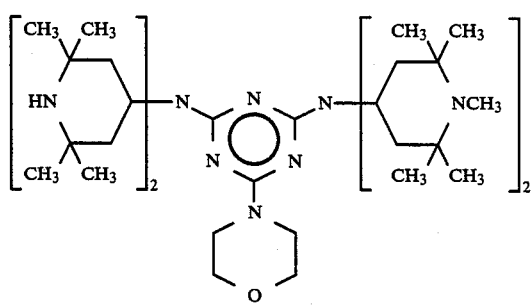
29.
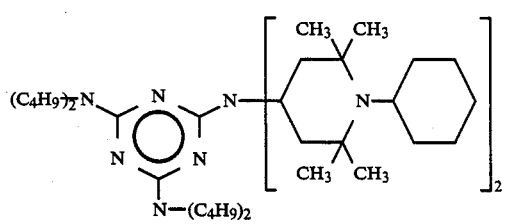
30.

-continued

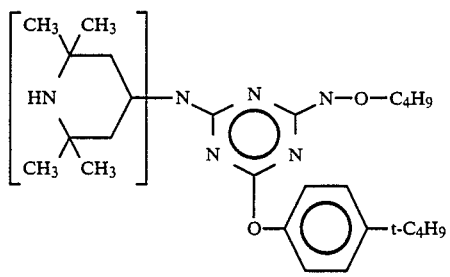
31.

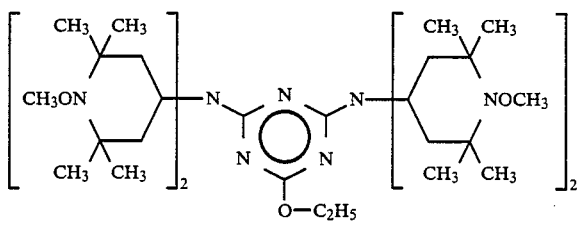
32.

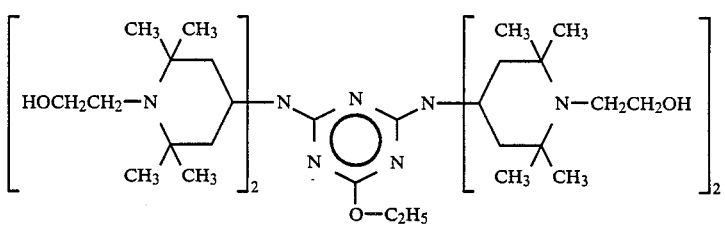
33.

These compounds are easily prepared by known procedures, reacting cyanuric chloride with the corresponding 2,2,6,6-tetramethyl piperidine compound, followed by reaction with amines, alcohols or phenols as required to complete the molecule. Alternatively, the cyanuric chloride can be reacted with the corresponding amine, alcohol or phenol followed by reaction with the corresponding 2,2,6,6-tetramethyl piperidyl compound.

The following Examples illustrate the procedure.

EXAMPLE I

Preparation of

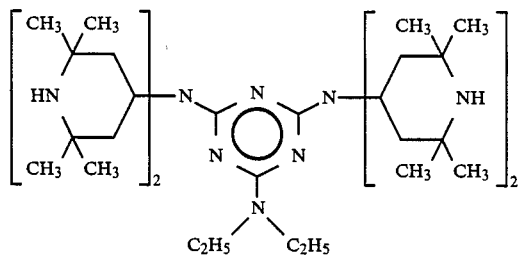

2,4-Dichloro-6-diethylaminotriazine 2.21 g and bis(2,2,6,6-tetramethyl-4-piperidyl)amine 5.90 g were dissolved in 25 ml of xylene. Powdered sodium hydroxide 0.88 g and sodium iodied 0.45 g were added and the mixture then stirred for 30 hours under reflux.

Following completion of the reaction, the solution was washed with water and then dried. The solvent was distilled off and n-hexane added, from which a white powder was recovered by crystallization and evaporation. The white powder melted at 210° to 212° C.

EXAMPLE II

Preparation of

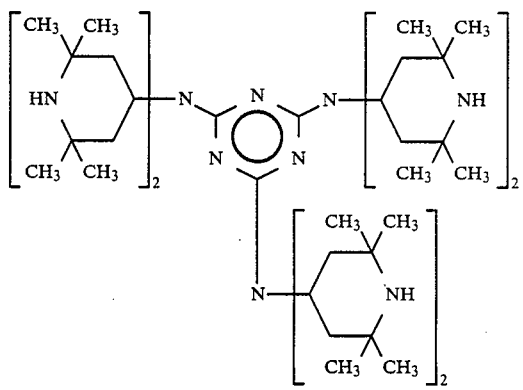

Bis(2,2,6,6-tetramethyl-4-piperidyl)amine 6.20 g was dissolved in 25 ml of xylene and powdered sodium hydroxide 0.93 g and cyanuric chloride 1.29 g added with cooling in an ice-water bath. Then, sodium iodide 0.42 g was added and the reaction mixture stirred for 20 hours under reflux. At the completion of the reaction, the solution was washed with water and then dried. The solvent was distilled off and n-hexane added. A white powder was recovered by crystallization from hexane. The powder sublimed at 363° C.

The polypiperidylamino triazines of this invention are effective light stabilizers for polymeric materials that are subject to deterioration when exposed to light. Small amounts are effective. An amount within the range from about 0.001 to about 5 parts, preferably from 0.01 to 3 parts, by weight per 100 parts by weight of polymer is usually sufficient. Larger amounts can be used, if desired.

Synthetic resins that can have their resistance to deterioration enhanced with the polypiperidylamino triazines according to this invention include α-olefin polymers such as polyethylene, polypropylene, polybutene, poly-3-methylbutene, or mixtures thereof, and copolymers with other monomers such as ethylene-vinyl acetate copolymer; ethylene-propylene copolymer; polystyrene; polyvinyl acetate; polyacrylic esters; copolymers from styrene and another monomer (for example, maleic anhydride, butadiene, and acrylonitrile); acrylonitrile-butadiene-styrene copolymer, acrylic acid ester-butadiene-styrene copolymer, methacrylic acid ester-butadiene-styrene copolymer, polymethacrylate esters such as polymethacrylate; polyvinyl alcohol; polyvinyl formal; polyvinyl butyral; linear polyesters, polyamides; polycarbonates; polyacetals; polyurethanes; cellulosic resins; phenol-formaldehyde resins; urea-formaldehyde resins; melamine-formaldehyde resins; epoxy resins; unsaturated polyester resins; silicone resins; halogen containing resins such as polyvinyl chloride, polyvinylidene chloride, polyvinylidene fluoride, and copolymers thereof, and rubbers such as isoprene rubber, butadiene rubber, epichlorohydrin rubber, chloroprene rubber, and blends of any of the above.

The polypiperidylamino triazines of the invention can be combined with conventional heat stabilizers such as phenolic antioxidants, polyvalent metal salts of organic acids, organic phosphites, thioethers, and other known heat stabilizers, thereby constituting light and heat stabilizer compositions of the invention.

The phenolic antioxidant contains one or more phenolic hydroxyl groups, and one or more phenolic nuclei, and can contain from about eight to about three hundred carbon atoms. In addition, the phenolic nucleus can contain an oxy or thio ether group.

The alkyl-substituted phenols and polynuclear phenols, because of their molecular weight, have a higher boiling point, and therefore are preferred because of their lower volatility. There can be one or a plurality of alkyl groups of one or more carbon atoms. The alkyl group or groups including any alkylene groups between phenol nuclei preferably aggregate at least four carbon atoms. The longer the alkyl or alkylene chain, the better the compatibility with polypropylene, inasmuch as the phenolic compound then acquires more of an aliphatic hydrocarbon character, and therefore there is no upper limit on the number of alkyl carbon atoms. Usually, from the standpoint of availability, the compound will not have more than about eighteen carbon atoms in an alkyl, alicyclidene and alkylene group, and a total of not over about fifty carbon atoms. The compounds may have from one to four alkyl radicals per phenol nucleus.

The phenol contains at least one and preferably at least two phenolic hydroxyls, the two or more hydroxyls being in the same ring, if there is only one. In the case of bicyclic phenols, the rings can be linked by thio or oxyether groups, or by alkylene, alicyclidene or arylidene groups.

The monocyclic phenols which can be employed have the structure:

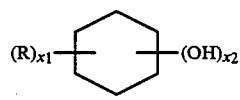

R is selected from the group consisting of hydrogen; halogen; and organic radicals containing from one to about thirty carbon atoms, such as alkyl, aryl, alkenyl, alkaryl, aralkyl, cycloalkenyl, cycloalkyl, alkoxy, and acyl

where R' is aryl, alkyl or cycloalkyl.

$x_1$ and $x_2$ are integers from one to four, and the sum of $x_1$ and $x_2$ does not exceed six.

The polycyclic phenol phenol is one having at least two aromatic nuclei linked by a polyvalent linking radical, as defined by the formula:

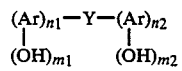

wherein

Y is a polyvalent linking group selected from the group consisting of oxygen; carbonyl; sulfur; sulfinyl; aromatic, aliphatic and cycloaliphatic hydrocarbon groups; and oxyhydrocarbon, thiohydrocarbon and heterocyclic groups. The linking group can have from one up to twenty carbon atoms.

Ar is a phenolic nucleus which can be a phenyl or a polycarbocyclic group having condensed or separate phenyl rings; each Ar group contains at least one free phenolic hydroxyl group up to a total of five. The Ar rings can also include additional rings connected by additional linking nuclei of the type Y, for example, Ar—Y—Ar—Y—Ar.

$m_1$ and $m_2$ are numbers from one to five, and $n_1$ and $n_2$ are numbers of one or greater, and preferably from one to four.

The aromatic nucleus Ar can, in addition to phenolic hydroxyl groups, include one or more inert substituents. Examples of such inert substituents include hydrogen, halogen atoms, e.g., chlorine, bromine and fluorine; organic radicals containing from one to about thirty carbon atoms, such as alkyl, aryl, alkaryl, aralkyl, cycloalkenyl, cycloalkyl, alkoxy, aryloxy and acyloxy

where R' is aryl, alkyl or cycloalkyl, or thiohydrocarbon groups having from one to about thirty carbon atoms, and carboxyl

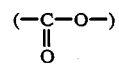

groups. Usually, however, each aromatic nucleus will not have more than about eighteen carbon atoms in any hydrocarbon substituent group. The Ar group can have from one to four substituent groups per nucleus.

Typical aromatic nuclei include phenyl, naphthyl, phenanthryl, triphenylenyl, anthracenyl, pyrenyl, chrysenyl, and fluoroenyl groups.

When Ar is a benzene nucleus, the polyhydric polycyclic phenol has the structure:

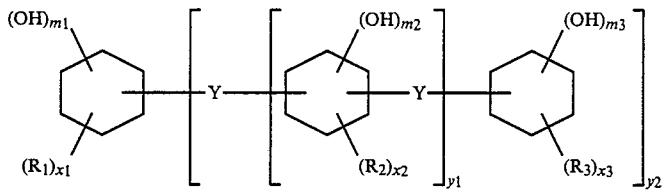

wherein

R$_1$, R$_2$ and R$_3$ are inert substituent groups as described in the previous paragraph;

m$_1$ and m$_3$ are integers from one to a maximum of five;

m$_2$ is an integer from one to a maximum of four;

x$_1$ and x$_3$ are integers from zero to four, and x$_2$ is an integer from zero to three;

y$_1$ is an integer from zero to about six and y$_2$ is an integer from one to five, preferably one or two.

Preferably, the hydroxyl groups are located ortho and/or para to Y.

Exemplary Y groups are alkylene, alkylidene, and alkenylene; arylene, alkyl arylene, arylalkylene; cycloalkylene, cycloalkylidene; and oxa-and thia-substituted such groups; tetrahydrofuranes, esters and triazino groups. The Y groups are usually bi, tri, or tetravalent, connecting two, three or four Ar groups. However, higher valency Y groups connecting more than four Ar groups, can also be used. According to their constitution, the Y groups can be assigned to subgenera as follows:

(1) Y groups where at least on carbon in a chain or cyclic arrangement connect the aromatic groups, such as:

—CH$_2$—CH$_2$—; —(CH$_2$)$_5$—; —CH$_2$—;

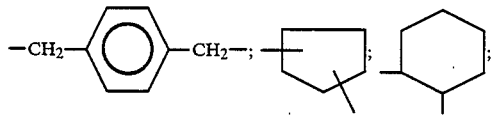

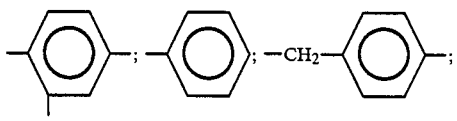

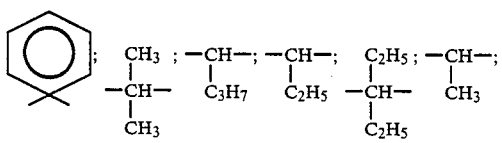

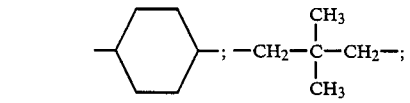

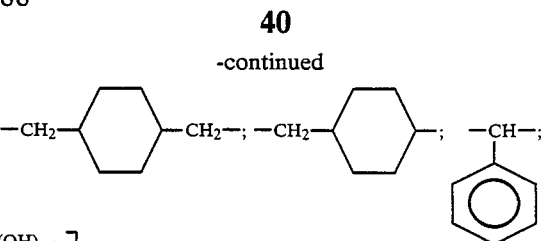

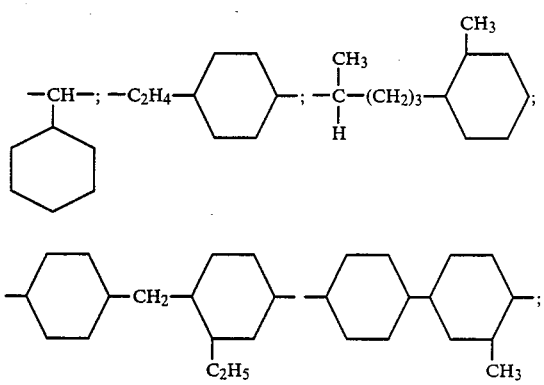

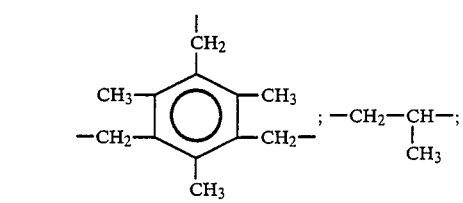

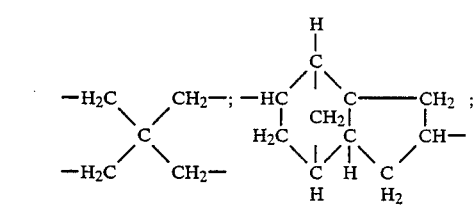

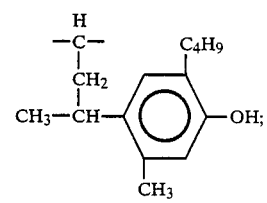

(2) Y groups where only atoms other than carbon link the aromatic rings, such as —O—, —S—,

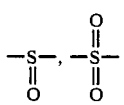

and —(S)$_x$— where x is a number from one to ten;

(3) Y groups made up of more than a single atom including both carbon and other atoms linking the aromatic nuclei, such as:

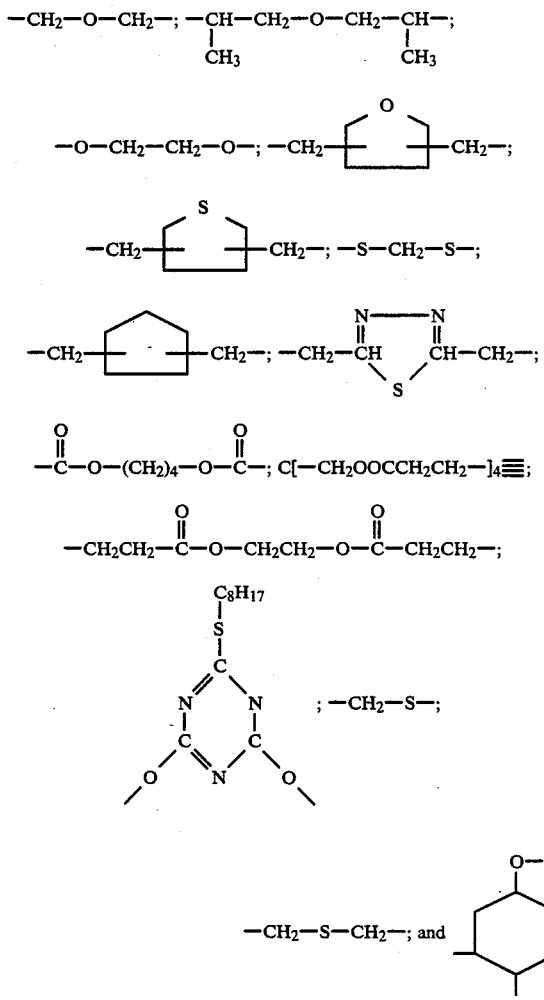

Although the relation of effectiveness to chemical structure is insufficiently understood, many of the most effective phenols have Y groups of subgenus (1), and accordingly this is preferred. Some of these phenols can be prepared by the alkylation of phenols or alkyl phenols with polyunsaturated hydrocarbons such as dicylopentadiene or butadiene.

Representative phenols include guaiacol, resorcinol monoacetate, vanillin, butyl salicylate, 2,6-di-tert-butyl-4-methyl phenol, 2-tert-butyl-4-methoxy phenol, 2,4-dinonyl phenol, 2,3,4,5-tetradecyl phenol, tetrahydro-α-naphthol, o-, m- and p-cresol, o-, m- and p-phenyl-phenol, o-, m- and p-xylenols, the carvenols, symmetrical xylenol, thymol, o-, m- and p-nonylphenol, o-, m- and p-dodecyl-phenol, and o-, m- and p-octyl-phenol, o-, and m-tert-butyl-p-hydroxy-anisole, p-n-decyloxy-phenol, p-n-decyloxy-cresol, nonyl-n-decyloxy-cresol, eugenol, isoeugenol, glyceryl monosalicylate, methyl-p-hydroxy-cinnamate, 4-benzyloxy-phenol, p-acetylaminophenol, p-stearyl-aminophenol, methyl-p-hydroxybenzoate, p-dichlorobenzoyl-aminophenol, p-hydroxysalicyl anilide, stearyl-(3,5-di-methyl-4-hydroxy-benzyl)thioglycolate, stearyl-β-(4-hydroxy-3,5-di-t-butylphenyl)propionate, distearyl-3,5-di-t-butyl-4-hydroxybenzylphosphonate, and distearyl (4-hydroxy-3-methyl-5-t-butyl)benzylmalonate.

Exemplary polyhydric phenols are orcinol, propyl gallate, catechol, resorcinol, 4-octyl-resorcinol, 4-dodecylresorcinol, 4-octadecyl-catechol, 4-isooctyl-phloroglucinol, pyrogallol, hexahydroxybenzene, 4-isohexylcatechol, 2,6-di-tertiary-butyl-resorcinol, 2,6-di-isopropyl-phloroglucinol.

Exemplary polyhydric polycyclic phenols are methylene bis-(2,6-di-tertiary-butyl-phenol), 2,2-bis-(4-hydroxy phenyl)-propane, methylene-bis-(p-cresol), 4,4'-benzylidene bis (2-tertiary-butyl-5-methyl-phenol), 4,4'-cyclo-hexylidene bis-(2-tertiary-butylphenol), 2,2'-methylene-bis-(4-methyl-6-(1'-methyl-cyclohexyl)-phenol), 2,6-bis-(2'-hydroxy-3'-tertiary-butyl-5'-methyl-benzyl)-4-methylphenol, 4,4'-bis-(2-tertiary-butyl-5-methyl-phenol), 2,2'-bis-(4-hydroxy-phenyl)butane, ethylene bis-(p-cresol), 4,4'-oxobis-phenol, 4,4'-oxobis-(3-methyl-5-isopropyl-phenol), 4,4'-oxobis-(3-methyl-phenol), 2,2'-oxobis-(4-dodecyl-phenol), 2,2'-oxobis-(4-methyl-5-tertiary-butyl-phenol), 4,4'-thio-bis-phenol; 4,4'-thio-bis-(3-methyl-6-tertiary-butyl-phenol, 2,2'-thio-bis-(4-methyl-6-tertiary-butyl-phenol), 4,4'-n-butylidene-(2-t-butyl-5-methyl-phenol), 2,2'-methylene-bis-(4-methyl-6-(1'-methyl-cyclohexyl)-phenol), 4,4'-cyclohexylene bis-(2-tertiary-butyl-phenol), 2,6-bis(2'-hydroxy-3'-t-butyl-5'-methyl-benzyl)-4-methyl-phenol, 4,4'-oxobis (naphthalene-1,5-diol), 1,3'-bis-(naphthalene-2,5-diol)propane, and 2,2'-butylene bis-(naphthalene-2,7-diol), (3-methyl-5-tert-butyl-4-hydroxy-phenyl)-4'-hydroxy-phenyl) propane, 2,2'-methylene-bis-(4-methyl-5-isopropylphenol), 2,2'-methylene-bis-(4-methyl-5-isopropylphenol), 2,2'-methylene-bis-(5-tert-butyl-4-chlorophenol), (3,5-di-tert-butyl-4-hydroxyphenyl)-(4'-hydroxyphenyl)ethane, (2-hydroxyphenyl)-(3',5'-di-tert-butyl-4',4-hydroxyphenyl)ethane, 2,2'-methylene-bis-(4-octylphenol), 4,4'-propylene-bis-(2-tert-butyl-phenol), 2,2'-isobutylene-bis-(4-nonyl-phenol), 2,4-bis-(4-hydroxy-3-t-butyl-phenoxy)-6-(n-octylthio)-1,3,5-triazine, 2,4,6-tris-(4-hydroxy-3-t-butyl-phenoxy)-1,3,5-triazine, 2,2'-bis-(3-t-butyl-4-hydroxy-phenyl)thiazolo-(5,4-d) thiazole, 2,2'-bis-(3-methyl-5-t-butyl-4-hydroxyphenyl)thiazolo-(5,4-d)-thiazole, 4,4'-bis-(4-hydroxyphenyl)pentanoic acid octadecyl ester, cyclopentylene-4,4'-bis-phenol, 2-ethylbutylene-4,4'-bisphenol, 4,4'-cyclooctylene-bis-(2-cyclohexylphenol), β,β-thiodiethanol-bis-(3-tert-butyl-4-hydroxyphenoxy acetate), 1,4-butanedio-bis-(3-tert-butyl-4-hydroxy-phenoxy acetate), pentaerythritol tetra-(4-hydroxy-phenol propionate), 2,4,4'-tri-hydroxy benzophenone, bis-(2-tert-butyl-3-hydroxy-5-methylphenyl) sulfide, bis-(2-tert-butyl-4-hydroxy-5-methylphenyl)sulfide, bis-(2-tert-butyl-4-hydroxy-5-methylphenyl)sulfoxide, bis-(3-ethyl-5-tert-butyl-4-hydroxybenzyl)sulfide, bis-(2-hydroxy-4-methyl-6-tert-butyl-phenyl)sulfide, 4,4'-bis-(4-hydroxyphenol)pentanoic acid octadecyl thiopropionate ester, 1,1,3-tris-(2'-methyl-4-hydroxy-5'-tert-butylphenyl)butane, 1,1,3-tris-(1-methyl-3-hydroxy-4-tert-butylphenyl)butane, 1,8-bis-(2-hydroxy-5-methyl-benzoyl-n-octane, 2,2'-ethylene-bis-[4'-(3-tert-butyl-4-hydroxyphenyl)-thiazole], 1-methyl-3-(3-methyl-5-tert-butyl-4-hydroxybenzyl)-naphthalene, 2,2'-(2-butene)-bis-(4-methoxy-6-tert-butylphenol)-bis-[3,3-bis-(4-hydroxy-3-t-butylphenyl)butyric acid]glycol ester, 4,4'-butylidene-bis-(6-t-butyl-m-cresol), 1,1,3-tris-(2-methyl-4-hydroxy-5-t-butylphenyl)butane, 1,3,5-tris-(3,5-di-t-butyl-4-hydroxybenzyl)-2,4,6--

-trimethylbenzene, tetrakis [methylene-3 (3,5-di-t-butyl-4-hydroxyphenyl)propionate]methane, 1,3,5-tris-(3,5-di-t-butyl-4-hydroxybenzyl)isocyanurate, 1,3,5-tris-(3,5-di-t-butyl-4-hydroxyphenyl)propionyl-oxyethyl isocyanurate, 2-octylthio-4,6-di-(4-hydroxy-3,5-di-t-butyl)-phenoxy-1,3,5-triazine, 4,4'-thiobis-(6-t-butyl-m-cresol) and pentaerythritol hydroxyphenyl propionate.

A particularly desirable class of polyhydric polycyclic phenols are the dicylopentadiene polyphenols, which are of the type:

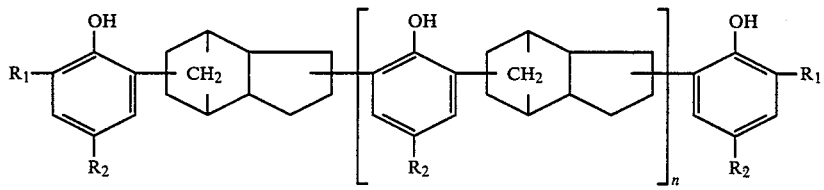

in which $R_1$ and $R_2$ are lower alkyl and can be the same or different, and n is the number of the groups enclosed by the brackets, and is usually from 1 to about 5. These are described in U.S. Pat. No. 3,567,683, dated Mar. 2, 1971 to Spacht. A commercially available member of this class is Wingstay L, exemplified by dicyclopentadiene tri-(2-tert-butyl-4-methyl-phenol) of the formula:

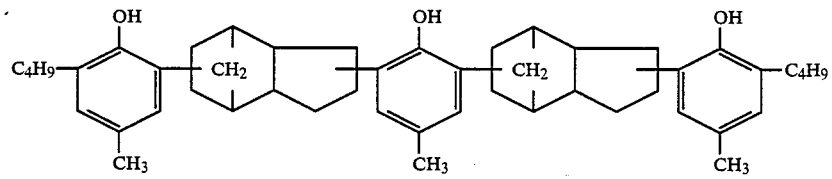

The polyhydric polycyclic phenols used in the invention can also be condensation products of phenols or alkylphenols with hydrocarbons having a bicyclic ring structure and a double bond or two or more double bonds, such as α-pinene, β-pinene, dipentene, limonene, vinylcyclohexene, dicylopentadiene, allo-ocimene, isoprene and butadiene. These condensation products are usually obtained under acidic conditions in the form of more or less complex mixtures of monomeric and polymeric compounds. However, it is usually not necessary to isolate the individual constituents. The entire reaction product, merely freed from the acidic condensation catalyst and unchanged starting material, can be used with excellent results. While the exact structure of these phenolic condensation products is uncertain, the Y groups linking the phenolic nuclei all fall into the preferred subgenus 1. For method of preparation, see e.g., U.S. Pat. No. 3,124,555, U.S. Pat. No. 3,242,135, and Bristish patent No. 961,504.

When the stabilizer composition is used in conjunction with a polyvalent metal salt of an organic acid, the organic acid will ordinarily have from about six to about twenty-four carbon atoms. The polyvalent metal can be any metal of Group II of the Periodic Table, such as zinc, calcium, cadmium, barium, magnesium and strontium. The alkali metal salts and heavy metal salts such as lead salts are unsatisfactory. The acid can be any organic non-nitrogenous monocarboxylic acid having from six to twenty-four carbon atoms. The aliphatic, aromatic, alicyclic and oxygen-containing heterocyclic organic acids are operable as a class. By the term "aliphatic acid" is meant any open chain carboxylic acid, substituted, if desired, with nonreactive groups, such as halogen, sulfur and hydroxyl. By the term "alicyclic" it will be understood that there is intended any cyclic acid in which the ring is nonaromatic and composed solely of carbon atoms, and such acids may if desired have inert, nonreactive substituents such as halogen, hydroxyl, alkyl radicals, alkenyl radicals and other carbocyclic ring structures condensed therewith. The oxygen-containing heterocyclic compounds can be aromatic or nonaromatic and can include oxygen and carbon in the ring structure, such as alkylsubstituted furoic acid. The aromatic acids likewise can have nonreactive ring substituents such as halogen, alkyl and alkenyl groups, and other saturated or aromatic rings condensed therewith.

As exemplary of the acids which can be used in the form of their metal salts there can be mentioned the following: hexoic acid, 2-ethylhexoic acid, n-octoic acid, isooctoic acid, capric acid, undecylic acid, lauric acid, myristic acid, palmitic acid, margaric acid, stearic acid, oleic acid, ricinoleic acid, behenic acid, chlorocaproic acid, hydroxy capric acid, benzoic acid, phenylacetic acid, butyl benzoic acid, ethyl benzoic acid, propyl benzoic acid, hexyl benzoic acid, salicylic acid, naphthoic acid, 1-naphthalene acetic acid, orthobenzoyl benzoic acid, naphthenic acids derived from petroleum, abietic acid, dihydroabietic acid, hexahydrobenzoic acid, and methyl furoic acid.

The water-insoluble salts are preferred, because they are not leached out when the plastic is in contact with water. Where these salts are not known, they are made by the usual types of reactions, such as by mixing the acid, or anhydride with the corresponding oxide or hydroxide of the metal in a liquid solvent, and heating, if necessary, until salt formation is complete.

A variety of organic triphosphites and acid phosphites can be employed, of which the following are exemplary.

the organic triphosphite can be any organic phosphite having three or more organic radicals attached to phosphorus through oxygen. The acid phosphite can be any organic phosphite having one or two organic radicals attached to phosphorus through oxygen. These radicals can be monovalent radicals, in the case of the triphosphites, diphosphites and monophisphites.

The organic triphosphites in which the radicals are monovalent radicals can be defined by the formula:

$$R_1-O-P-O-R_3$$
$$|$$
$$O$$
$$|$$
$$R_2$$

in which $R_1$, $R_2$ and $R_3$ are selected from the group consisting of alkyl, alkenyl, aryl, alkaryl, aralkyl, and cycloalkyl groups having from one to about thirty carbon atoms.

The acid phosphites are defined by the same formula, but one or two of $R_1$, $R_2$ and $R_3$ is hydrogen or a cation of a metal or ammonium.

Also included are the organic triphosphites having a bivalent organic radical forming a heterocyclic ring with the phosphorus of the type:

$$R_4 \begin{matrix} O \\ \diagup \\ \diagdown \\ O \end{matrix} P-O-R_5$$

in which $R_4$ is a bivalent organic radical selected from the group consisting of alkylene, arylene, aralkylene, alkarylene and cycloalkylene radicals having from two to about thirty carbon atoms, and $R_5$ is a monovalent organic radical as defined above in the case of $R_1$, $R_2$ and $R_3$;

$R_5$ is hydrogen or a cation, in the case of the acid phosphites.

Also useful organic triphosphites are mixed heterocyclic-open chain phosphites of the type:

$$R_4 \begin{matrix} O \\ \diagup \\ \diagdown \\ O \end{matrix} P-O-R_4-O-P \begin{matrix} O \\ \diagup \\ \diagdown \\ O \end{matrix} R_4$$

More complex triphosphites are formed from trivalent organic radicals, of the type:

$$R_6-O-P\begin{matrix}O\\ \diagup \\ \diagdown \\ O\end{matrix} HO-R_6\begin{matrix}O\\ \diagup \\ \diagdown \\ O\end{matrix}P-O-R_6\begin{matrix}O\\ \diagup \\ \diagdown \\ O\end{matrix}P-O-R_6\begin{matrix}OH\\ \diagup \\ \diagdown \\ OH\end{matrix}$$

in which $R_6$ is a trivalent organic radical of any of the types of $R_1$ to $R_5$, inclusive, as defined above.

A particularly useful class of complex triphosphites are the tetraoxadiphosphaspiro undecanes of the formula:

$$R_1-O-P\begin{matrix}OCH_2\\ \diagup \\ \diagdown \\ OCH_2\end{matrix}C\begin{matrix}CH_2O\\ \diagup \\ \diagdown \\ CH_2O\end{matrix}P-O-R_2$$

where $R_1$ and $R_2$ are selected from the group consisting of aryl, alkyl, aryloxyethyl, alkyloxyethyl, aryloxyethoxyethyl, alkyloxyethoxyethyl and alkyloxypolyethoxyethyl having from about 1 to about 30 carbon atoms.

In the case of the acid phosphites, one or both of $R_1$ and $R_2$ is also hydrogen or a cation.

An especially preferred class of organic triphosphites and acid phosphites have a bicyclic aromatic group attached to phosphorus through oxygen, with no or one or more phenolic hydroxyl groups on either or both of the aromatic rings. These phosphites are characterized by the formula;

$$Z\begin{matrix}O\\ \diagdown \\ \diagup \\ O\end{matrix}P-OArO-P\begin{matrix}O\\ \diagup \\ \diagdown \\ O\end{matrix}Z$$

or $$(HO)_m-Ar-O-P\begin{matrix}O\\ \diagup \\ \diagdown \\ O\end{matrix}Z.$$

in which

Ar is a mono or bicyclic aromatic nucleus and m is an integer of from 0 to about 5. Z is one or a plurality of organic radicals as defined above for $R_1$ to $R_6$, taken singly or together in sufficient number to satisfy the valences of the two phosphite oxygen atoms.

One or both Z radicals is also hydrogen, in the case of the acid phosphites, and can include additional bicyclic aromatic groups of the type $(HO)_m-Ar$.

The cation in the case of acid phosphites can be a metal, such as an alkali metal, for instance, sodium, potassium or lithium; an alkaline earth metal, for instance, barium, calcium, or a nontoxic polyvalent metal, such as magnesium, tin and zinc.

Usually, the triphosphites and acid phosphites will not have more than about sixty carbon atoms.

Exemplary triphosphites are monophenyl di-2-ethylhexyl phosphite, diphenyl mono-2-ethylhexyl phosphite, di-isooctyl monotolyl phosphite, tri-2-ethylhexyl phosphite, phenyl dicyclohexyl phosphite, phenyl diethyl phosphite, triphenyl phosphite, tricresyl phosphite, tri(dimethylphenyl) phosphite, trioctadecyl phosphite, triisooctyl phosphite, tridodecyl phosphite, isooctyl diphenyl phosphite, diisooctyl phenyl phosphite, tri(t-octylphenyl) phosphite, tri-(t-nonylphenyl) phosphite, benzyl methyl isopropyl phosphite, butyl dicresyl phosphite, isooctyl di(octylphenyl) phosphite, di(2-ethylhexyl) (isooctylphenyl) phosphite, tri (2-cyclohexylphenyl) phosphite), tri-α-naphthyl phosphite, tri (phenylphenyl) phosphite, tri(2-phenylethyl) phosphite, ethylene phenyl phosphite, ethylene t-butyl phosphite, ethylene isohexyl phosphite, ethylene isooctyl phosphite, ethylene cyclohexyl phosphite, 2-phenoxy-1,3,2-dioxaphosphorinane, 2-butoxy-1,3,2-dioxyphosphorinane, 2-octoxy-5,5-dimethyl-dioxaphosphorinane, and 2-cyclohexyloxy-5,5-diethyl dioxaphosphorinane.

Exemplary pentaerythritol triphosphites are 3,9-diphenoxy-2,4,8,10-tetraoxa-3,9-diphosphaspiro-(5,5)-undecane (diphenyl-pentaerythritol diphosphite), 3,9-di(decyloxy)-2,4,8,10-tetraoxa-3,9-diphosphaspiro (5,5)-undecane, 3,9-di(isodecyloxy)-2,4,8,10-tetraoxa-3,9-diphosphaspiro-(5,5)-undecane, 3,9-di(octadecyloxy)-2,4,8,10-tetraoxa-3,9-diphosphaspiro-(5,5)-undecane, 3-phenoxy-9-isodecyloxy-2,4,8,10-tetraoxa-3,9-diphosphaspiro-(5,5)-undecane, 3,9-di(methoxy)-2,4,8,10-tetraoxa-3,9-diphosphaspiro-(5,5)-undecane, 3,9-di(lauryloxy)-2,4,8,10-tetraoxa-3,9-diphosphaspiro-(5,5)-undecane, 3,9-di-p-tolyloxy-2,4,8,10-tetraoxa-3,9-diphosphaspiro-(5,5)-undecane, 3,9-di(methoxyethyloxy)-2,4,8,10-tetraoxa-3,9-diphosphaspiro-(5,5)-undecane, 3-methoxyethyloxy-9-isodecyloxy-2,4,8,10-tetraoxa-3,9-diphosphaspiro-(5,5)-undecane, 3,9-di(ethoxyethyloxy)-2,4,8,10-tetraoxa-3,9-diphosphaspiro-(5,5)-undecane, 3,9-di(butoxyethyloxy)-2,4,8,10-tetraoxa-3,9-diphosphaspiro-(5,5)-undecane, 3-methoxyethyloxy-9-butoxy-ethyloxy-2,4,8,10-tetraoxa-3,9-diphosphaspiro-(5,5)-undecane, 3,9-di(methoxyethoxyethyloxy)-2,4,8,10-tetraoxa-3,9-diphosphaspiro-(5,5)-undecane, 3,9-di(butoxyethoxyethyloxy)-2,4,8,10-tetraoxa-3,9-diphosphaspiro-(5,5)-undecane, 3,9-di(methoxyethoxyethyloxy)-2,4,8,10-tetraoxa-3,9-diphosphaspiro-(5,5)-undecane, 3,9-di(methoxy (polyethoxy)ethyloxy)-2,4,8,10-tetraoxa-3,9-diphosphaspiro-(5,5)-undecane where the (polyethoxy) ethyloxy group has an average molecular weight of 350), 3,9-di(methoxy(polyethoxy)ethyloxy)-2,4,8,10-tetraoxa-3,9-diphosphaspiro-(5,5)-undecane (where the (polyethoxy) ethyloxy group has an average molecular weight of 550).

Exemplary of the bis aryl triphosphites are: bis(4,4'-thio-bis(2-tertiary-butyl-5-methyl-phenol)) isooctyl phosphite, mono(4,4'-thio-bis(2-tertiary-butyl-5-methyl-phenol)) di-phenyl phosphite, tri-(4,4'-n-butylidene-bis(2-tertiary-butyl-5-methylphenol)) phosphite, (4,4'-benzylidene-bis(2-tertiary-butyl-5-methyl-phenol)) di-phenyl phosphite, isooctyl 2,2'-bis(-parahydroxyphenyl) propane phosphite, decyl 4,4'-n-butylidene-bis (2-tertiary-butyl-5-methylphenol) phosphite, tri-4,4'-thiol-bis (2-tertiary-butyl-5-methylphenol) phosphite, 2-ethylhexyl-2,2'-methylene-bis(4-methyl-6,1'-methylcyclohexyl) phenol phosphite, tri(2,2'-bis-(para-hydroxyphenyl) propane) phosphite, tri(4,4'-thio-bis(2-tertiary-butyl-5-methyl-phenol) phosphite, isooctyl-(2,6-bis(2'-hydroxy-3,5-dinonylbenzyl)-4-nonyl phenyl)) phosphite, tetra-tridecyl-4,4'-n-butylidene-bis(2-tertiary-butyl-5-methylphenyl) phosphite, tetra-isooctyl-4,4'-thio-bis(2-tertiary-butyl-5-methylphenyl) diphosphite, 2,2-methylene-bis(4-methyl-6,1'-methyl cyclohexyl phenyl) polyphosphite, isooctyl-4,4'-isopropylidene-bisphenyl polyphosphite, 2-ethylhexyl-2,2'-methylene-bis(4-methyl-6,1'-methyl-cyclohexyl) phenyl triphosphite, tetra-tridecyl-4,4'-oxydiphenyl diphosphite, tetra-n-dodecyl-4,4'-n-butylidene bis (2-tertiary-butyl-5-methylphenyl) diphosphite, tetra-tridecyl-4,4'-isopropylidene bisphenyl diphosphite, hexa-tridecyl butane-1,1,3-tris(2'-methyl-5'-tetriary-butylphenyl-4') triphosphite.

Exemplary acid phosphites are di(phenyl) phosphite, monophenyl phosphite, mono(diphenyl) phosphite, dicresyl phosphite, di-(o-isooctylphenyl) phosphite, di(p-ethylhexylphenyl) phosphite, di(p-t-octylphenyl) phosphite, di(dimethylphenyl) phosphite, di-n-butyl phosphite, di-2-ethylhexyl phosphite, mono-2-ethylhexylphosphite, diisooctyl phosphite, monoisooctyl phosphite, monododecyl phosphite, 2-ethylhexyl phenyl phosphite, 2-ethylhexyl-(n-octylphenyl) phosphite, monocyclohexyl phosphite, dicyclohexyl phosphite, di(2-cyclohexyl phenyl) phosphite, di-α-naphthyl phosphite, diphenyl phenyl phosphite, di(diphenyl) phosphite, di-(2-phenyl ethyl) phosphite, dibenzyl phosphite, monobenzyl phosphite, n-butyl cresyl phosphite and didodecyl phosphite, cresyl phosphite, t-octylphenyl phosphite, ethylene phosphite, butyl cresyl phosphite, isooctyl monotolyl phosphite and phenyl cyclohexyl phosphite.

Exemplary of the bis aryl phosphites are: bis(4,4'-thio-bis(2-tertiary-butyl-5-methylphenol)) phosphite, (4,4'-thio-bis(2-tertiary-butyl-5-methylphenol)) phenyl phosphite, bis(4,4'-butylidene-bis(2-tertiary-butyl-5-methylphenol)) phosphite, mono(4,4'-benzylidene-bis(2-tertiary-butyl5-methylphenol)) phosphite, mono(2,2'-bis-(parahydroxyphenyl) propane) phosphite, mono(4,4'-butylidene-bis(2-tertiary-butyl-5-methylphenol) phosphite, bis(4,4'-thio-bis(2-tertiary-butyl-5-methylphenol)) phosphite, mono-2-ethylhexyl-mono-2,2'-methylene-bis(4-methyl-6,1'-methylcyclohexyl) phenol phosphite, bis (2,2'-para-hydroxyphenyl)propane) phosphite, monoisooctylmono(4,4'-thio-bis(2-tertiary-butyl-5-methylphenol)) phosphite, isooctyl-(2,6-bis(2'-hydroxy-3,5-dinonylbenzyl)-4-nonylphenyl)) phosphite, tri-tridecyl-4,4'-n-butylidene-bis(2-tertiary-butyl5-methylphenyl) diphosphite, triisooctyl-4,4'-thio-bis(2-tertiary-butyl-5-methylphenyl) diphosphite, bis(2,2'-methylene-bis(4-methyl-6,1'-methyl cyclohexyl phenyl)) phosphite, isooctyl-4,4'-isopropylidene-bisphenyl phosphite, monophenyl mono(2,2'-methylene-bis(4-methyl-6,1'-methyl-cyclohexyl)) triphosphite, di-tridecyl-4,4'-oxydiphenyl diphosphite, di-n-dodecyl-4,4'-n-butylidene-bis(2-tertiary-butyl-5-methylphenyl) diphosphite, di-tridecyl-4,4'-isopropylidene bisphenyl diphosphite, tetra-tridecyl butane-1,1,3-tris(2'-methyl-5-tertiary-butylphenyl-4)-triphosphite.

The thiodipropionic acid ester has the following formula:

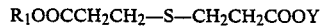

$R_1OOCCH_2CH_2-S-CH_2CH_2COOY$ in which $R_1$ is an organic radical selected from the group consisting of hydrocarbon radicals such as alkyl, alkenyl, aryl, cycloalkyl and mixed alkyl aryl and mixed alkyl cycloalkyl radicals; hydroxyalkyl and hydroxyalkyloxyalkylene radicals; and esters thereof with aliphatic carboxylic acids; and Y is selected from the group consisting of (a) hydrogen, (b) a second R radical $R_2$, which can be the same as or different from the $R_1$ radical, (c) a polymeric chain of n thiodipropionic acid ester units:

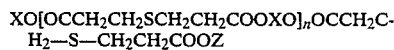

$XO[OCCH_2CH_2SCH_2CH_2COOXO]_nOCCH_2CH_2-S-CH_2CH_2COOZ$ where Z is hydrogen, $R_2$ or M, n is the number of thiodipropionic acid ester units in the chain, and X is a bivalent hydrocarbon group of the type of $R_1$, that is, alkylene, alkenylene, cycloalkylene, mixed alkylenearylene and mixed alklenecycloalkylene radicals; hydroxyalkylene and hydroxyalkyloxyalkylene radicals; and esters thereof with aliphatic carboxylic acids; the value of n can range upwards from 0, but there is no upper limit on n except as is governed by the ratio of carbon atoms to sulfur atoms as stated below; and (d) a polyvalent metal M of Group II of the periodic table such as zinc, calcium, cadmium, barium, magnesium and strontium.

The molecular weights of the R and Y radicals are taken such that with the remainder of the molecule the thiodipropionic ester has a total of from about ten to about sixty carbon atoms per sulfur atom.

Accordingly, the various thiodipropionic acid ester species coming with the above-designated categories within the general formula can be defined as follows:
(a) $R_1OOCCH_2CH_2SCH_2CH_2COOH$
(b) $R_1OOCCH_2CH_2SCH_2CH_2COOR_2$
(c) $R_1O[OCCH_2CH_2SCH_2CH_2COOX-O]_nOCCH_2CH_2SCH_2CH_2COOZ$
(d) $R_1OOCCH_2CH_2SCH_2CH_2COOM$ In the above formulae $R_1$ and $R_2$, M, X and Z are the same as before and the value of $n_1$ can range upwards from 1, but there is no upper limit on $n_1$ except as is imposed by the ratio of carbon atoms, as stated below. In the polymer (c), as in the other forms of thiodipropionic acid esters, the total number of carbon atoms per sulfur atom is within the range from about ten to about sixty.

The R radical of these esters is important in furnishing compatibility with the polymer. The Y radical is desirably a different radical, $R_2$ or M or a polymer, where R is rather low in molecular weight, so as to compensate for this in obtaining the optimum compatibility and nonvolatility. Where Y is a metal, the thiodipropionic acid ester furnishes the beneficial properties of the polyvalent metal salt which is described above.

The aryl, alkyl, alkenyl, and cycloalkyl groups may, if desired, contain inert, nonreactive substituents such as halogen and other carbocyclic and heterocyclic ring structures condensed therewith.

Typical R radicals are, for example, methyl, ethyl, propyl, isopropyl, butyl, isobutyl, t-butyl, amyl, isoamyl, n-octyl, isooctyl, 2-ethyl hexyl, t-octyl, decyl, dodecyl, octadecyl, allyl, hexenyl, linoleyl, ricinoleyl, oleyl, phenyl, xylyl, tolyl, ethylphenyl, naphthyl, cyclohexyl, benzyl, cyclopentyl, methylcyclohexyl, ethylcyclohexyl, and naphthenyl, hydroxyethyl, hydroxypropyl, glyceryl, sorbityl, pentaerythrityl, and polyoxyalkylene radicals such as those derived from diethylene glycol, triethylene glycol, polyoxypropylene glycol, polyoxyethylene glycol, and polyoxypropyleneoxyethylene glycol, and esters thereof with any of the organic acids named below in the discussion of the polyvalent metal salts, including in addition those organic acids having from two to five carbon atoms, such as acetic, propionic, butyric and valeric acids.

Typical X radicals are alkylene radicals such as ethylene, tetramethylene, hexamethylene, decamethylene, alkyl-substituted alkylene radicals such as 1,2-propylene,

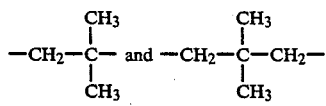

arylene radicals such as phenylene

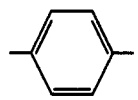

methylenephenylene

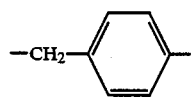

dimethylene phenylene

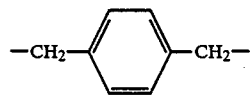

and alicyclylene such as cyclohexylene

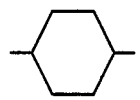

and cyclopentylene

As exemplary of the thiopropionic acid esters which can be used, there can be mentioned the following: monolauryl thiodipropionic acid, dilauryl thiodipropionate, butyl stearyl thiodipropionate, 2-ethylhexyl lauryl thiodipropionate, di-2-ethylhexyl-thiodipropionate, diisodecyl thiodipropionate, isodecyl phenyl thiodipropionate, benzyl lauryl thiodipropionate, benzyl phenyl thiodipropionate, the diester of mixed coconut fatty alcohols and thiodipropionic acid, the diester of mixed tallow fatty alcohols and thiodipropionic acid, the acid ester of mixed cottonseed oil fatty alcohols and thiodipropionic acid, the acid ester of mixed soyabean oil fatty alcohols and thiodipropionic acid, cyclohexyl nonyl thiodipropionate, monooleyl thiodipropionic acid, hydroxyethyl lauryl thiodipropionate, monoglyceryl thiodipropionic acid, glyceryl monostearate monothiodipropionate, sorbityl isodecyl thiodipropionate, the polyester of diethylene glycol and thiodipropionic acid, the polyester of triethylene glycol and thiodipropionic acid, the polyester of hexamethylene glycol and thiodipropionic acid, the polyester of pentaerythritol and thiodipropionic acid, the polyester of octamethylene glycol and thiodipropionic acid, the polyester of p-dibenzyl alcohol and thiodipropionic acid, ethylbenzyl lauryl thiodipropionate, strontium stearyl thiodipropionate, magnesium oleyl thiodipropionate, calcium dodecylbenzyl thiodipropionate, and mono(dodecylbenzyl) thiodipropionic acid.

These esters are for the most part known compounds, but where they are not available, they are readily prepared by esterification of thiodipropionic acid and the corresponding alcohol.

Also useful are:

(1) Thioalkanoic acid amides of Tokuno et al Japanese patent No. 16,286/68 having the formula:

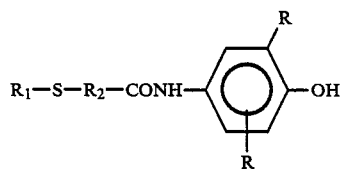

R is alkyl of one to eight carbon atoms, $R_1$ is alkyl of six to twenty-four carbon atoms, and $R_2$ is alkylene of one to six carbon atoms.

(2) Thioalkanoic acid amides of 1,3,5-triazines of Ozeki et al Japanese patent No. 20,366/68 having the formula:

$$R-S-C_2H_4-\underset{\underset{O}{\|}}{C}-N\diagup\diagdown\begin{matrix}N-\underset{\underset{}{\|}}{\overset{O}{\|}}C-C_2H_4-S-R\\ \\N-\underset{\underset{O}{\|}}{C}-C_2H_4-S-R\end{matrix}$$

R is alkyl of eight to eighteen carbon atoms.

(3) Bis-thioalkanoic acid amides of Yamamoto et al Japanese patent No. 23,765/68 having the formula:

$$R-S-C_2H_4-\underset{\underset{O}{\|}}{C}-NH-NH-\underset{\underset{O}{\|}}{C}-C_2H_4-S-R$$

R is alkyl of more than six carbon atoms, aryl or aralkyl.

(4) Bis-thioalkylanoic acid amides of Ozeki et al Japanese patent No. 26,184/69 having the formula:

$$R-S-C_2H_4-\underset{\underset{O}{\|}}{C}-NH-NH-\underset{\underset{O}{\|}}{C}-R_1-\underset{\underset{O}{\|}}{C}-NH-NH-\underset{\underset{O}{\|}}{C}-C_2H_4-S-R$$

R is alkyl of twelve to eighteen carbon atoms, and $R_1$ is alkylene of one to ten carbon atoms, cycloalkylene, or arylene.

(5) Bis-alkylene thioalkanoic acid amides of Ozeki Japanese patent No. 31,464/69 having the formula:

$$R-S-C_2H_4-\underset{\underset{O}{\|}}{C}-NH-CH_2-NH-\underset{\underset{O}{\|}}{C}-C_2H_4-S-R$$

R is alkyl of more than six carbon atoms, aryl, or aralkyl.

(6) Thioalkanoic acid amide derivatives of Minagawa et al, published Japanese application No. 106,484/74 having the formula:

$$R-S-C_2H_4-\underset{\underset{O}{\|}}{C}-NH-NH-\underset{\underset{O}{\|}}{C}-\underset{\underset{O}{\|}}{C}-NH-NH-\underset{\underset{O}{\|}}{C}-C_2H_4-S-R$$

R is hydrocarbyl of one to twenty carbon atoms.

(7) Alkylene bis-thioalkanoic acid amides of U.S. Pat. No. 4,279,805 to Ohzeki et al, patented July 21, 1981, having the general formula:

$$R_1-S-R_2-\underset{\underset{O}{\|}}{C}-NH-R_3-NH-\underset{\underset{O}{\|}}{C}-R_2-S-R_1$$

wherein:

$R_1$ is alkyl having from one to about fifty carbon atoms;

$R_2$ is alkylene having from one to about three carbon atoms; and $R_3$ is alkylene having from about two to about twelve carbon atoms.

β-Alkylthiopropionic acid esters havng the general formula:

$$R-S-C_2H_4COOR-(R')_n$$

wherein:

R is alkyl of four to twenty carbon atoms;

n is a number of from 1 to 6; and

R' is the residue of an alcohol havng from one to six hydroxyl groups.

Pentaerythritol tetra dodecyl thio propionate is an example of this group.

Other conventional light stabilizers can be employed, such as hydroxybenzophenones such as 2-hydroxy-4-methoxybenzophenone, 2-hydroxy-4-n-octoxy benzophenone, 2,4-dihydroxybenzophenone, benzotriazoles, such as 2-(2-hydroxy-5-methylphenyl) benzotriazoles, 2(2-hydroxy-3-t-butyl-5-methylphenyl)-5-chlorobenzotriazole, 2(2-hydroxy-3-5-di-t-butylphenyl) 5-chlorobenzotriazole, 2(2-hydroxy-3,5-di-t-amylphenyl) benzotriazole, benzoates such as phenylsalicylate, 2,4-di-t-butylphenyl-3',5-di-t-butyl-4-hydroxy phenylbenzoate, nickel compounds such as nickel-2,2'-thiobis(4-t-octyl-phenolate), nickel-monoethyl(3,5-di-t-butyl-4-hydroxybenzyl)phosphonate, substituted acrylonitriles such as methyl-α-cyano-β-methyl-β-(p-methoxy phenyl)acrylate and oxalic anilides such as N-2-ethyl phenyl-N'-2-ethoxy-5-t-butyl phenyl oxalic diamide, N-2-ethyl phenyl-N'-2-ethoxy phenyl oxalic diamide.

A sufficient amount of the stabilizer or combination is used to improve the resistance of the synthetic polymer to deterioration in physical properties when exposed to heat and light, including, for example, discoloration, reduction in melt viscosity and embrittlement. Very small amounts are usually adequate. Amounts within the range from about 0.001 to about 5% total stabilizers including the polypiperidylamino triazines of the invention by weight of the polymer are satisfactory. Preferably, from 0.01 to 3% is employed for optimum stabilization.

The stabilizer systems of the invention are readily rendered in solid particulate form, comprising a blend of:

(a) polypiperidylamino triazines light stabilizer in an amount of from about 10 to about 35 parts by weight; and optionally:

(b) a phenolic antioxidant in an amount from about 10 to about 35 parts by weight; and/or (c) other heat or light stabilizers in an amount of from about 10 to about 35 parts by weight.

The polypiperidylamino triazines light stabilizer of the invention can be employed in combination with phenolic antioxidant and/or other conventional heat and light stabilizers for the particular synthetic polymer.

Thus, for example, in the case of the polyvinyl chloride resins, other polyvinyl chloride resin heat stabilizers can be included, including polyvalent metal fatty acid salts such as barium and cadmium salts of the higher fatty acids; organotin compounds; and epoxy compounds; and organic phosphites.

With polyolefin resins there can be employed fatty acid salts of polyvalent metals, and the higher fatty acid esters of thiodipropionic acids, such as, for example, dilauryl thiodipropionate.

With polyamide resin compositions, polyamide stabilizers such as copper salts in combination with iodides and/or other phosphorus compounds and salts of divalent manganese can be used.

With synthetic rubbers and acrylonitrile-butadiene-styrene terpolymers, other antioxidants and polyvalent metal salts of the higher fatty acids can be used.

In addition, other conventional additives for synthetic polymers, such as plasticizers, lubricants, emulsifiers, antistatic agents, flame-proofing agents, pigments and fillers, can be employed.

The stabilizer or combination is incorporated in the polymer in suitable mixing equipment, such as a mill or a Banbury mixer. If the polymer has a melt viscosity which is too high for the desired use, the polymer can be worked until its melt viscosity has been reduced to the desired range before addition of the stabilizer. Mixing is continued until the mixture is substantially uniform. The resulting composition is then removed from the mixing equipment and brought to the size and shape desired for marketing or use.

The stabilized polymer can be worked into the desired shape, such as by milling, calendering, extruding or injection molding or fiber-forming. In such operations, it will be found to have a considerably improved resistance to reduction in melt viscosity during the heating, as well as a better resistance to discoloration and embrittlement on ageing and heating.

The following Examples represent preferred embodiments of synthetic polymer compositions containing the stabilizers in accordance with the invention.

EXAMPLES 1 TO 5

Polypropylene compositions were prepared using stabilizers of the invention and two stabilizers of the prior art, having the following formulation:

| Ingredient | Parts by Weight |
| --- | --- |
| Polypropylene | 100 |
| Stearyl-β-(3,5-di-t-butyl-4-hydroxyphenyl)propionate | 0.2 |
| Stabilizer as shown in Table I | 0.3 |

The compositions were thoroughly blended in a Brabender Plastograph, and then compression-molded to sheets 0.3 mm thick. Pieces 2.5 cm$^2$ were cut off from the sheets, and exposed to a high pressure mercury lamp, with and without immersion in hot water at 80° C. for 15 hours. The time in hours when degradation set in, as determined by a significant discoloration and/or embrittlement, was noted as hours to failure, and the results are set forth in Table I.

TABLE I

| | | Hours to Failure | |
| --- | --- | --- | --- |
| Example No. | Stabilizer | Without Immersion | After Immersion |
| Control 1 | 2-Ethoxy-4,6-bis(N,N—bis(2,2,6,6-tetramethyl-4-piperidyl)amino)-1,3,5-triazine | 390 | 280 |
| Control 2 | 2,4,6-Tris(N,N—bis(2,2,6,6-tetramethyl-4-piperidyl)amino)-1,3,5-triazine | 420 | 320 |
| Example 1 | 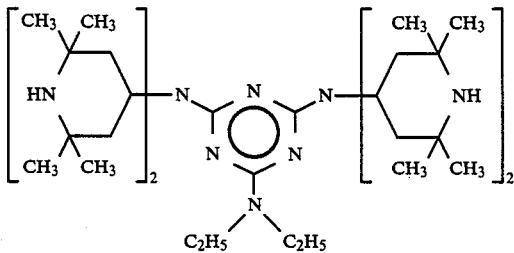 | 750 | 670 |
| Example 2 | 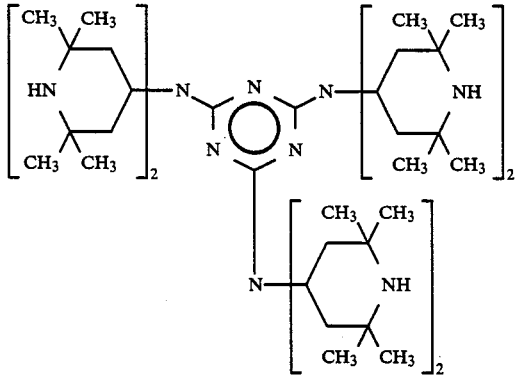 | 820 | 750 |

TABLE I-continued

| Example No. | Stabilizer | Hours to Failure Without Immersion | Hours to Failure After Immersion |
|---|---|---|---|
| Example 3 | 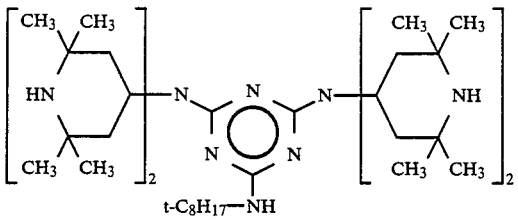 | 770 | 690 |
| Example 4 | 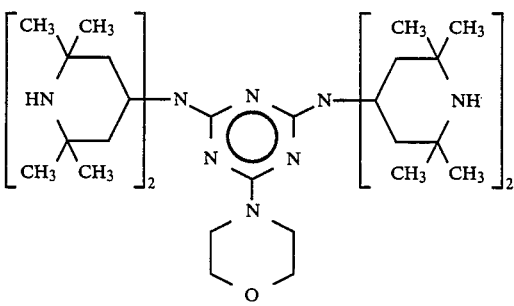 | 730 | 660 |
| Example 5 | 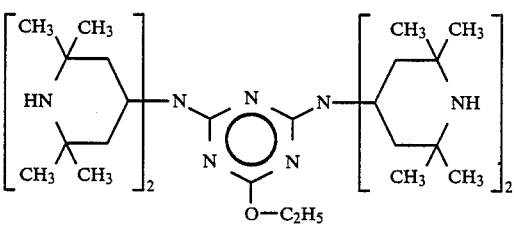 | 700 | 640 |

The improved stabilizing effectiveness of the compounds of the invention as compared to the compounds of the prior art is apparent from the above data.

EXAMPLES 6 TO 10

Conventional stabilizers for polymeric materials may lose their effectiveness because of volatilization or decomposition at the high polymer processing temperatures. This is not true of the stabilizers of the invention, as shown by observing the effect of heat in repeated extrusions of ethylene-propylene copolymer compositions.

The compostions were prepared using stabilizers of the invention and two stabilizers of the prior art, having the following formulation:

| Ingredient | Parts by Weight |
|---|---|
| Ethylene-propylene copolymer | 100 |
| Ca stearate | 0.2 |
| Stearyl-$\beta$-(3,5-di-t-butyl-4-hydroxyphenyl)propionate | 0.1 |
| Dilaurylthiodipropionate | 0.2 |
| Stabilizer as shown in Table II | 0.2 |

The compositions were mixed and then extruded 5 times at a cylinder temperature of 230° C. and 240° C., a head die temperature of 250° C., and a velocity of 20 rpm. The test pieces were then molded by injection molding at 250° C. The test pieces were exposed to a high pressure mercury lamp. The time in hours when degradation set in, as determined by a significant discoloration and/or embrittlement, was noted as hours to failure, and the results are set forth in Table II.

TABLE II

| Example No. | Stabilizer | Hours to Failure Extruded One Time | Hours to Failure Extruded Five Times |
|---|---|---|---|
| Control 1 | 2-Ethoxy-4,6-bis(N,N—bis(2,2,6,6-tetramethyl-4-piperidyl)amino)-1,3,5-triazine | 360 | 260 |
| Control 2 | 2,4,6-Tris(N,N—bis(2,2,6,6-tetramethyl-4-piperidyl)amino)-1,3,5-triazine | 400 | 290 |

TABLE II-continued

| Example No. | Stabilizer | Hours to Failure | |
|---|---|---|---|
| | | Extruded One Time | Extruded Five Times |
| Example 6 | [structure: bis(1,2,2,6,6-pentamethyl-4-piperidyl)amino triazine with N(C₄H₉)₂] | 580 | 510 |
| Example 7 | [structure: tris(2,2,6,6-tetramethyl-4-piperidylamino) triazine] | 620 | 550 |
| Example 8 | [structure: (C₄H₉)₂N-triazine-N(C₄H₉)₂ with piperidylamino group] | 510 | 440 |
| Example 9 | [structure: bis(2,2,6,6-tetramethyl-4-piperidylamino) triazine with O-phenyl-t-C₄H₉] | 530 | 450 |
| Example 10 | [structure: bis(N-acryloyl-2,2,6,6-tetramethyl-4-piperidylamino) triazine with O-C₂H₅] | 530 | 470 |

The improved stabilizing effectiveness of the compounds of the invention as compared to the compounds of the prior art is apparent from the above data.

High density polyethylene compositions were prepared using the stabilizers of the invention and two of the prior art, having the following formulation:

| Ingredient | Parts by Weight |
| --- | --- |
| High density polyethylene | 100 |
| Ca stearate | 1 |
| Tetrakis-(methylene-3-(3,5-di-t-butyl-4-hydroxyphenyl)propionate) methane | 0.1 |
| Distearyl thiodipropionate | 0.3 |

| Ingredient | Parts by Weight |
| --- | --- |
| Stabilizer as shown in Table III | 0.2 |

The stabilizers were blended with the polymer on a two-roll mill and sheets 0.5 mm thick were prepared by compression molding of the blend. Pieces 2.5 cm$^2$ were cut off from the sheets, and exposed in a Weather-O-Meter to ultraviolet light. The time in hours when degradation set in, as determined by a significant discoloration and/or embrittlement, was noted as hours to failure, and the results are set forth in Table III.

TABLE III

| Example No. | Stabilizer | Hours to Failure |
| --- | --- | --- |
| Control 1 | 2-Ethoxy-4,6-bis(N,N—bis(2,2,6,6-tetramethyl-4-piperidyl)amino)-1,3,5-triazine | 710 |
| Control 2 | 2,4,6-Tris(N,N—bis(2,2,6,6-tetramethyl-4-piperidyl)amino)-1,3,5-triazine | 750 |
| Example 11 | 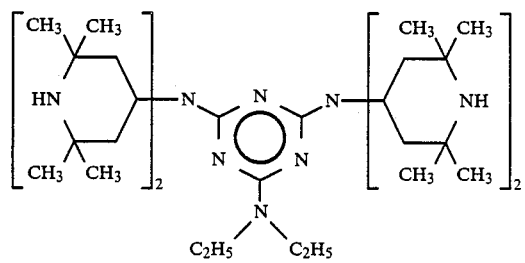 | 1120 |
| Example 12 | 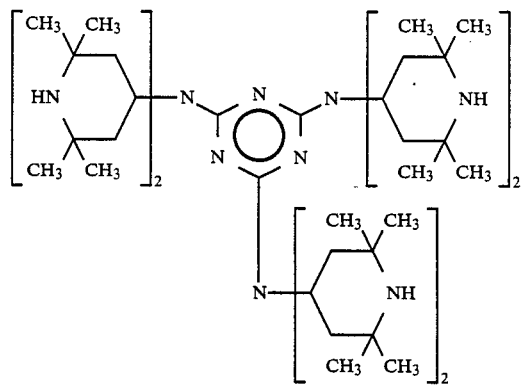 | 1180 |
| Example 13 | 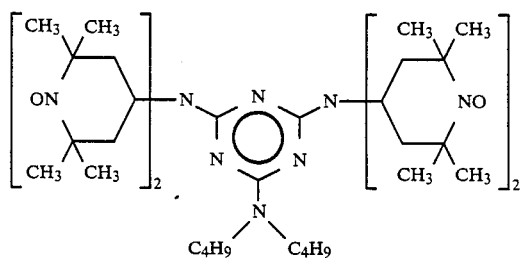 | 1050 |

TABLE III-continued

| Example No. | Stabilizer | Hours to Failure |
|---|---|---|
| Example 14 | [structure: bis(2,2,6,6-tetramethyl-4-piperidylamino) triazine with morpholino substituent] | 1100 |
| Example 15 | [structure: bis(2,2,6,6-tetramethyl-4-piperidylamino) triazine with O-C$_2$H$_5$ substituent] | 1020 |

The improved stabilizing effectiveness of the compounds of the invention as compared to the compounds of the prior art is apparent from the above data.

EXAMPLES 16 TO 20

Ethylene-vinyl acetate copolymer compositions were prepared using stabilizers of the invention and two stabilizers of the prior art, having the following formulation:

| Ingredient | Parts by Weight |
|---|---|
| Ethylene-vinyl acetate copolymer | 100 |
| 2,6-Di-t-butyl-p-cresol | 0.1 |
| Ca stearate | 0.1 |
| Zn stearate | 0.1 |
| Diisodecylphenyl phosphite | 0.2 |
| Stabilizer as shown in Table IV | 0.2 |

The stabilizers were blended with the polymer on a two-roll mill at 130° C. Sheets 0.4 mm thick were then compression-molded at 140° C. from the resulting blend. Pieces 2.5 cm$^2$ were cut off from the sheets, and exposed to ultraviolet light in a Weather-O-Meter for 500 hours. Tensile strength of the sheet samples were determined before and at the conclusion of the test. The results are shown in Table IV as percent retention of the initially-determined tensile strength.

TABLE IV

| Example No. | Stabilizer | % Retention of Tensile Strength |
|---|---|---|
| Control 1 | 2-Ethoxy-4,6-bis(N,N—bis(2,2,6,6-tetramethyl-4-piperidyl)amino)-1,3,5-triazine | 62 |
| Control 2 | 2,4,6-Tris(N,N—bis(2,2,6,6-tetramethyl-4-piperidyl)amino)-1,3,5-triazine | 65 |
| Example 16 | [structure: bis(2,2,6,6-tetramethyl-4-piperidylamino) triazine with N(C$_2$H$_5$)$_2$ substituent] | 78 |

TABLE IV-continued

| Example No. | Stabilizer | % Retention of Tensile Strength |
|---|---|---|
| Example 17 | [structure] | 76 |
| Example 18 | [structure] | 80 |
| Example 19 | [structure] | 78 |
| Example 20 | [structure] | 75 |

The improved stabilizing effectiveness of the compounds of the invention as compared to the compounds of the prior art is apparent from the above data.

EXAMPLES 21 TO 25

Polyvinyl chloride resin compositions were prepared having the following formulation, utilizing stabilizers in accordance with the invention and stabilizers of the prior art:

| Ingredient | Parts by Weight |
|---|---|
| Polyvinyl chloride | 100 |
| Dioctyl phthalate | 48 |
| Epoxidized soybean oil | 2 |
| Tris(nonyl phenyl)phosphite | 0.2 |
| Ca stearate | 1.0 |
| Zn stearate | 0.1 |
| Stabilizer as shown in Table V | 0.3 |

The stabilizers were mixed with the polyvinyl chloride on a two-roll mill and then sheeted off to form sheets 1 mm thick. The light resistance of the sheets was determined by placing strips 1 cm wide in a Weather-O-Meter, and exposing them to ultraviolet light. The time required for the sheets to develop a noticeable discoloration and/or embrittlement, indicating deterioration due to oxidation in the presence of ultraviolet light, was then noted in hours as the hours to failure. The following results were obtained.

TABLE V

| Example No. | Stabilizer | Hours to Failure |
|---|---|---|
| Control 1 | 2-Ethoxy-4,6-bis(N,N—bis(2,2,6,6-tetramethyl-4-piperidyl)amino)-1,3,5-triazine | 500 |
| Control 2 | 2,4,6-Tris(N,N—bis(2,2,6,6-tetramethyl-4-piperidyl)amino)-1,3,5-triazine | 520 |
| Example 21 | 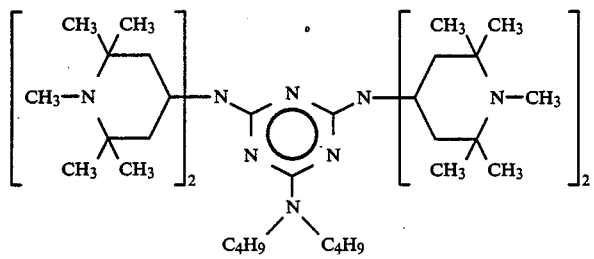 | 760 |
| Example 22 | 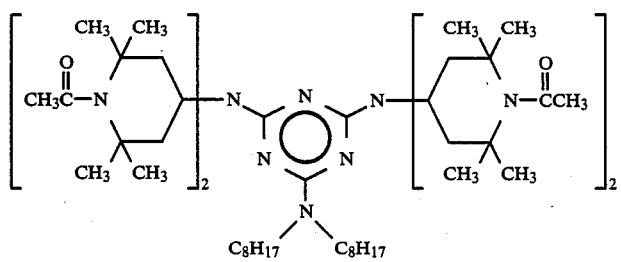 | 730 |
| Example 23 | 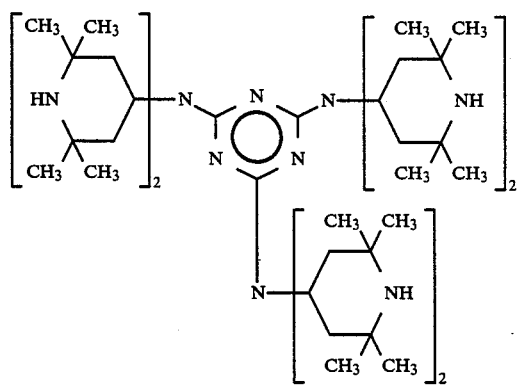 | 770 |
| Example 24 | 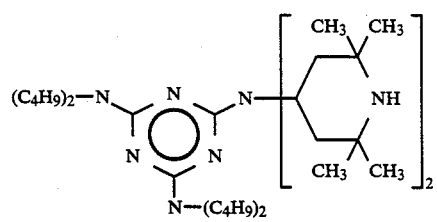 | 700 |
| Example 25 | | 720 |

TABLE V-continued

| Example No. | Stabilizer | Hours to Failure |
|---|---|---|

[structure: bis-piperidyl triazine with acrylamide groups and O—C₂H₅ substituent]

The improved stabilizing effectiveness of the compounds of the invention as compared to the compounds of the prior art is apparent from the above data.

EXAMPLES 26 TO 30

Acrylonitrile-butadiene-styrene terpolymer resin compositions were prepared, using stabilizers of the invention and of the prior art, with the following formulation:

| Ingredient | Parts by Weight |
|---|---|
| Acrylonitrile-butadiene-styrene terpolymer | 100 |
| 4,4-Butylidene-bis(2-t-butyl-m-cresol) | 0.1 |
| Stabilizer as shown in Table VI | 0.3 |

The stabilizers were blended with the resin on a two-roll mill, and sheets 3 mm thick were prepared by compression molding of the resulting blend. Pieces 2.5 cm² were cut off from the sheets and subjected to ultraviolet light in a Weather-O-Meter for 800 hours. The tensile strength of the strips was determined before and after the text exposure, and the results are reported in Table VI as the percent of tensile strength retained at the end of the test.

TABLE VI

| Example No. | Stabilizer | % Retention of Tensile Strength |
|---|---|---|
| Control 1 | 2-Ethoxy-4,6-bis)N,N—bis(2,2,6,6-tetramethyl-4-piperidyl)amino)-1,3,5-triazine | 61 |
| Control 2 | 2,4,6-Tris(N,N—bis(2,2,6,6-tetramethyl-4-piperidyl)amino)-1,3,5-triazine | 64 |
| Example 26 | | 78 |

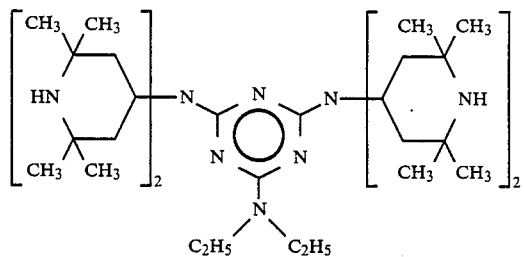

| Example 27 | | 80 |

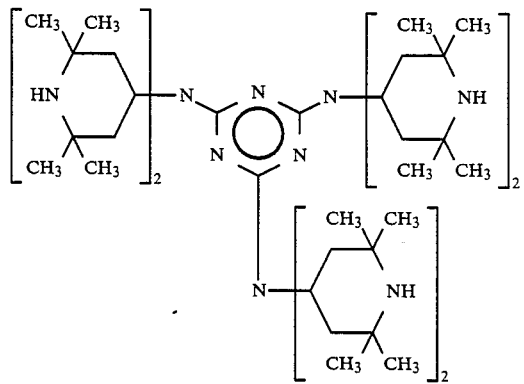

TABLE VI-continued

| Example No. | Stabilizer | % Retention of Tensile Strength |
|---|---|---|
| Example 28 | | 75 |

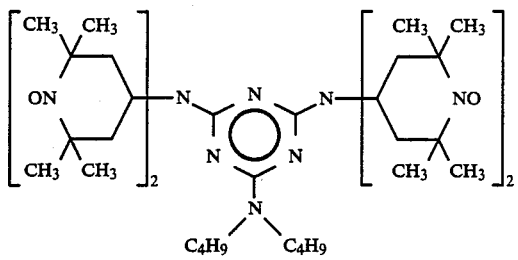

| | | |
|---|---|---|
| Example 29 | | 77 |

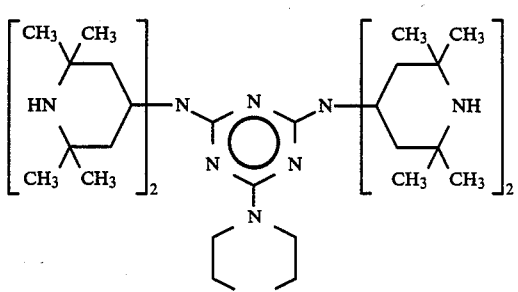

| | | |
|---|---|---|
| Example 30 | | 75 |

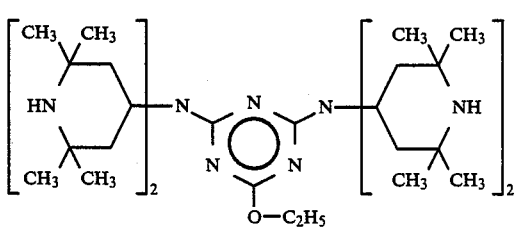

The improved stabilizing effectiveness of the compounds of the invention as compared to the compounds of the prior art is apparent from the above data.

EXAMPLES 31 TO 35

Polyurethane resin compositions were prepared using stabilizers of the invention and of the prior art, having the following formulation:

| Ingredient | Parts by Weight |
|---|---|
| Polyurethane resin (Asahi Denka U-100) | 100 |
| Ba stearate | 0.7 |
| Zn stearate | 0.3 |

| Ingredient | Parts by Weight |
|---|---|
| 2,6-di-t-butyl-p-cresol | 0.1 |
| Stabilizer as shown in Table VII | 0.3 |

The stabilizers were blended with the finely powdered polyurethane resin on a two-roll mill for five minutes at 70° C., and then sheeted off. The sheet was compression molded at 120° C. for 5 minutes to form sheets 0.5 mm thick. Pieces 2.5 cm$^2$ were cut out from the sheets and exposed to ultraviolet light in a Weather-O-Meter for fifty hours. Elongation before and after exposure was determined, and the percent elongation retained after the exposure is given in Table VII.

TABLE VII

| Example No. | Stabilizer | % Retention of Elongation |
|---|---|---|
| Control 1 | 2-Ethoxy-4,6-bis(N,N—bis(2,2,6,6-tetramethyl-4-piperidyl)amino)-1,3,5-triazine | 55 |
| Control 2 | 2,4,6-Tris(N,N—bis(2,2,6,6-tetramethyl-4-piperidyl)amino)-1,3,5-triazine | 58 |
| Example 31 | | |

TABLE VII-continued
| Example No. | Stabilizer | % Retention of Elongation |
|---|---|---|
| | 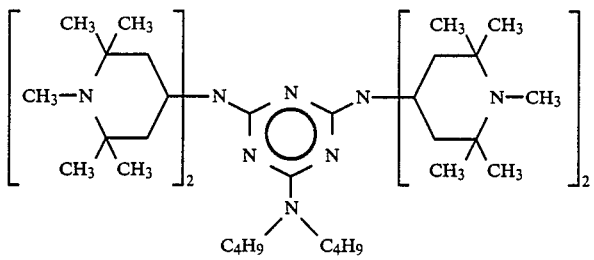 | |
| Example 32 | | 78 |
| | 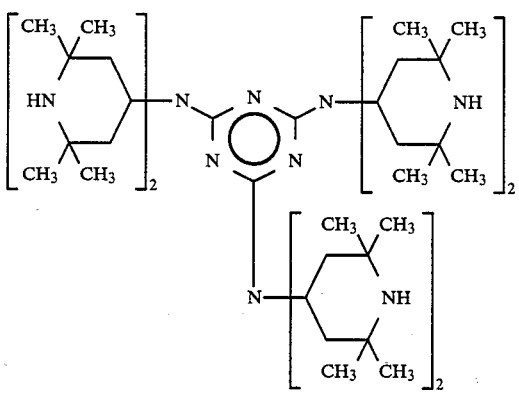 | |
| Example 33 | | 74 |
| | 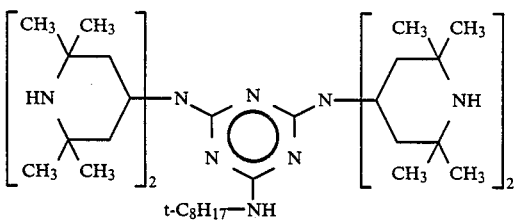 | |
| Example 34 | | 71 |
| | 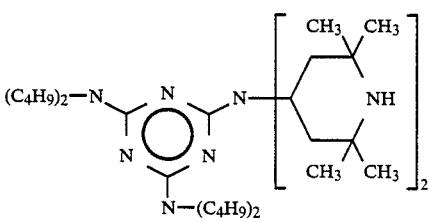 | |
| Example 35 | | 72 |

TABLE VII-continued

| Example No. | Stabilizer | % Retention of Elongation |
|---|---|---|

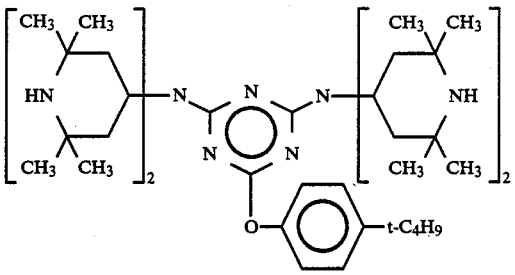

The improved stabilizing effectiveness of the compounds of the invention as compared to the compounds of the prior art is apparent from the above data.

EXAMPLES 36 TO 40

The stabilizers of this invention are effective light stabilizers for synthetic polymer coating compositions, particularly acrylic lacquers. This is demonstrated by the following experiments.

The effect of the stabilizer in a two-coat metallic effect finish comprising metallic effect priming lacquer and unpigmented finishing lacquer was determined.

(a) Metallic effect priming lacquer

Methyl methacrylate, 100 g, n butylacrylate, 66 g, 2-hydroxyethyl-methacrylate, 30 g, methacrylic acid, 4 g, xylene, 80 g, and n-butanol, 20 g, were heated with stirring at 110° C. while adding a solution of azo-bis-isobutyronitrile, 2 g, dodecylmercaptan, 0.5 g, xylene, 80 g, and n-butanol, 20 g, added dropwise over 3 hours. The solution was then stirred an additional two hours at 110° C.

The resulting acrylic resin solution, 12 parts, was then made into a metallic effect priming lacquer by mixing it with butoxylated methylol melamine (Mitsui Toatsu Co., Yuban 20SE60; solids content 60%) 2.5 parts, cellulose acetobutyrate (20% butylacetate solution) 50 parts, aluminum pigment (Toyo Aluminum Co., Alpaste 1123N) 5.5 parts, xylene 10 parts, butyl acetate, 20 parts, and copper phthalocyanine blue, 0.2 part.

(b) Unpigmented finishing lacquer

An inpigmented finishing lacquer was then prepared by mixing 48 parts of the acrylic resin solution with butoxylated methylol melamine, 10 parts, xylene, 10 parts, butoxyethylacetate, 1 part, and the stabilizer shown in Table VIII, 0.15 part.

Pieces of steel sheeting which were coated with a primer were first coated with the priming lacquer and then with the finishing lacquer. The priming lacquer was sprayed on to a thickness of about 20 μ and aired for 10 minutes. Then the clear lacquer was sprayed on to a thickness of about 30 μ. After airing for 15 minutes the samples were stoved for 30 minutes at 140° C.

The coated sheets were exposed to ultraviolet light in a Weather-O-Meter. The time in hours when degradation set in, determined by cracking on the surface of the sheet, was noted as hours to failure. The results are shown in Table VIII.

TABLE VIII

| Example No. | Stabilizer | Hours to Failure |
|---|---|---|
| Control 1 | None | 1600 |
| Control 2 | 2-Ethoxy-4,6-bis(N,N—bis(2,2,6,6-tetramethyl-4-piperidyl)amino)-1,3,5-triazine | 1900 |
| Control 3 | 2,4,6-Tris(N,N—bis(2,2,6,6-tetramethyl-4-piperidyl)amino)-1,3,5-triazine | 2100 |
| Example 36 | | 3000 |
| Example 37 | 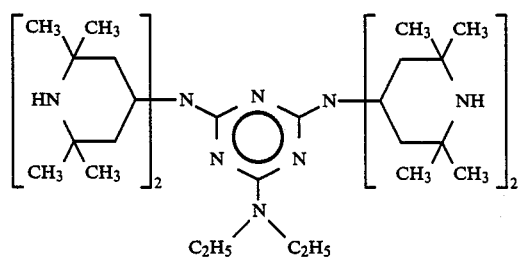 | 2800 |

TABLE VIII-continued

| Example No. | Stabilizer | Hours to Failure |
|---|---|---|
| Example 38 | [structure with two 2,2,6,6-tetramethylpiperidyl groups bearing N-acetyl, linked to triazine with N(C8H17)2] | 3300 |
| Example 39 | [tris-piperidylamino triazine structure with NH groups] | 3000 |
| Example 40 | [structure with t-C8H17—NH on triazine] | 2700 |
| | [structure with CH2=CHC(O)—N acryl groups and O—C2H5 on triazine] | |

The improved stabilizing effectiveness of the compounds of the invention as compared to the compounds of the prior art is apparent from the above data.

Having regard to the foregoing disclosure, the following is claimed as the inventive and patentable embodiments thereof:

1. A stabilizer composition for enhancing the resistance of synthetic polymers to deterioration upon exposure to light and heat comprising a poly(2,2,6,6-tetramethyl piperidyl amino)-1,3,5-triazine having the formula:

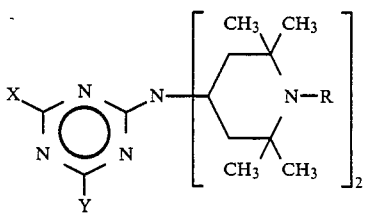

in which:

R is selected from the group consisting of hydrogen; alkyl, alkenyl, cycloalkyl, hydroxyalkyl and alkoxy having from one to about twelve carbon atoms; acyl having from about one to about twelve carbon atoms; and oxyl;

X and Y are each selected from the group consisting of

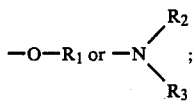

wherein:

$R_1$ is selected from the group consisting of alkyl, hydroxyalkyl and alkylenealkoxy having from one to about twelve carbon atoms; cycloalkyl having from three to about twelve carbon atoms; and aryl having from six to about eighteen carbon atoms;

$R_2$ and $R_3$ are selected from the group consisting of hydrogen; alkyl having from one to about twelve carbon atoms; cycloalkyl having from three to about twelve carbon atoms; and aryl having from six to about eighteen carbon atoms; and $R_2$ and $R_3$ taken together as alkylene in a five to six member ring including the nitrogen atom in the ring; and

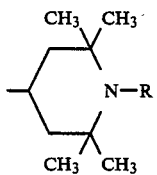

and at least one synthetic polymer heat stabilizer selected from the group consisting of phenolic antioxidants, organic phosphites, polyvalent metal salts and thiodipropionic acid esters.

2. A stabilizer composition according to claim 1 in which the heat stabilizer is a phenolic antioxidant.

3. A stabilizer composition according to claim 1 in which the heat stabilizer is an organic phosphite.

4. A stabilizer composition according to claim 1 in which the heat stabilizer is a polyvalent metal salt.

5. A stabilizer composition according to claim 1 in which the heat stabilizer is a thiodipropionic acid ester.

* * * * *